(12) United States Patent
Jackson et al.

(10) Patent No.: US 12,714,468 B2
(45) Date of Patent: Aug. 25, 2026

(54) BONE ANCHOR RECEIVER UPRIGHT ARMS AND CLOSURES HAVING HELICALLY WOUND THREADS TO APPLY THRUST WITH CONTROLLED SPLAY

(71) Applicant: Roger P. Jackson, Prairie Village, KS (US)

(72) Inventors: Roger P. Jackson, Prairie Village, KS (US); James L. Surber, Kansas City, KS (US)

( * ) Notice: Subject to any disclaimer, the term of this patent is extended or adjusted under 35 U.S.C. 154(b) by 0 days.

(21) Appl. No.: 18/504,004

(22) Filed: Nov. 7, 2023

(65) Prior Publication Data

US 2024/0065733 A1 Feb. 29, 2024

Related U.S. Application Data

(60) Division of application No. 17/750,153, filed on May 20, 2022, now Pat. No. 12,527,602, which is a continuation of application No. 16/905,621, filed on Jun. 18, 2020, now abandoned, which is a continuation of application No. 16/391,049, filed on Apr. 22, 2019, now Pat. No. 10,687,855, which is a continuation of application No. 15/689,080, filed on Aug. 29, 2017, now Pat. No. 10,265,102, which is a continuation of application No. 14/567,217, filed on Dec. 11, 2014, now Pat. No. 9,770,265, which is a continuation of application No. 14/086,728, filed on Nov. 21, 2013, now Pat. No. 8,911,478.

(60) Provisional application No. 61/851,300, filed on Mar. 5, 2013, provisional application No. 61/796,859, filed on Nov. 21, 2012.

(51) Int. Cl.
*A61B 17/70* (2006.01)
*A61B 17/68* (2006.01)
*A61B 90/00* (2016.01)

(52) U.S. Cl.
CPC ........ *A61B 17/7002* (2013.01); *A61B 17/683* (2013.01); *A61B 17/7032* (2013.01); *A61B 17/7035* (2013.01); *A61B 17/7052* (2013.01); *A61B 2090/037* (2016.02)

(58) Field of Classification Search
None
See application file for complete search history.

(56) References Cited

U.S. PATENT DOCUMENTS

| | | | | |
|---|---|---|---|---|
| 2006/0009773 A1* | 1/2006 | Jackson | F16B 35/047 606/301 |
| 2006/0058794 A1* | 3/2006 | Jackson | A61B 17/7032 606/272 |
| 2006/0084993 A1* | 4/2006 | Landry | A61B 17/7032 606/279 |
| 2007/0083199 A1* | 4/2007 | Baccelli | A61B 17/7056 606/273 |
| 2008/0288002 A1* | 11/2008 | Crall | A61B 17/7038 606/301 |
| 2010/0181762 A1* | 7/2010 | Carcagno | E21B 17/042 285/334 |
| 2016/0206350 A1* | 7/2016 | Keyer | A61B 17/7007 |

* cited by examiner

*Primary Examiner* — Tessa M Matthews
(74) *Attorney, Agent, or Firm* — Polsinelli PC

(57) ABSTRACT

Bone anchor receiver upright arms and closures have threads for controlling splay.

22 Claims, 11 Drawing Sheets

A
53
118
116
19
47
51
42
106
46
18
110
130
64
104
20
126
132
134
127

20
18
53
104
126
144
A
144
142
112
132
19
54
130
47
64
49
48
55
D1
D2
R1
42
61
D
R2
51
51
47
56
57
55
60
P
60
H1
H2
49
62
66
127
146
114
134
110
106
64
66

47
19
48
49
54
55
56
57
T
60
R
61
L
X
D2
D1
51
42
62
64
18
66

121
112
116
144
53
20
118
123
126
19
142
118
146
118
119
119
18
140
116
42
46

18
121
112
116
20
116
42
104
142
19
146
116
118
144
53
123
121
116
42
140
121
123
116
126
116

110
104
42
46
18
106
19
20
46
127

146
140
53
A
18
19
20
110
132
42
12
12
43
106
127
21
11
11
17
17
16
16
14
B
10
15
8
23
4
1
6
44
43
126
130
53
18
12
12
11
11
19
20
42
17
134
106
127
21
22
16
16
10
14
8

Fig. 17.
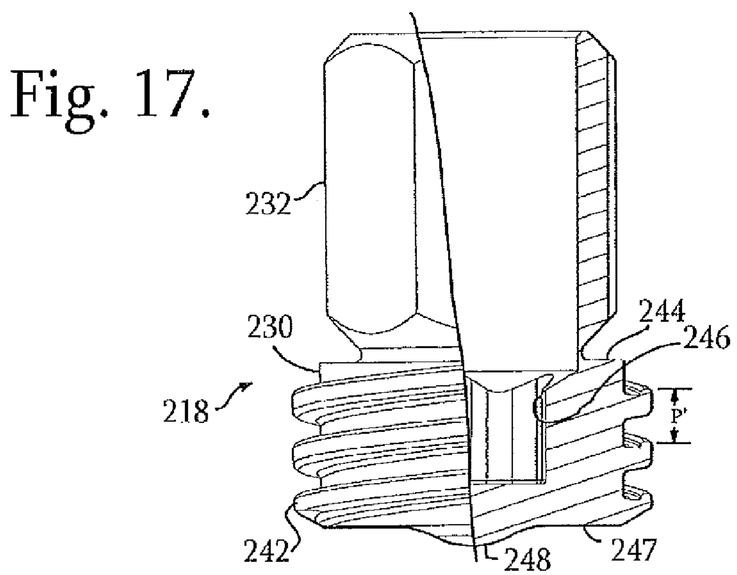
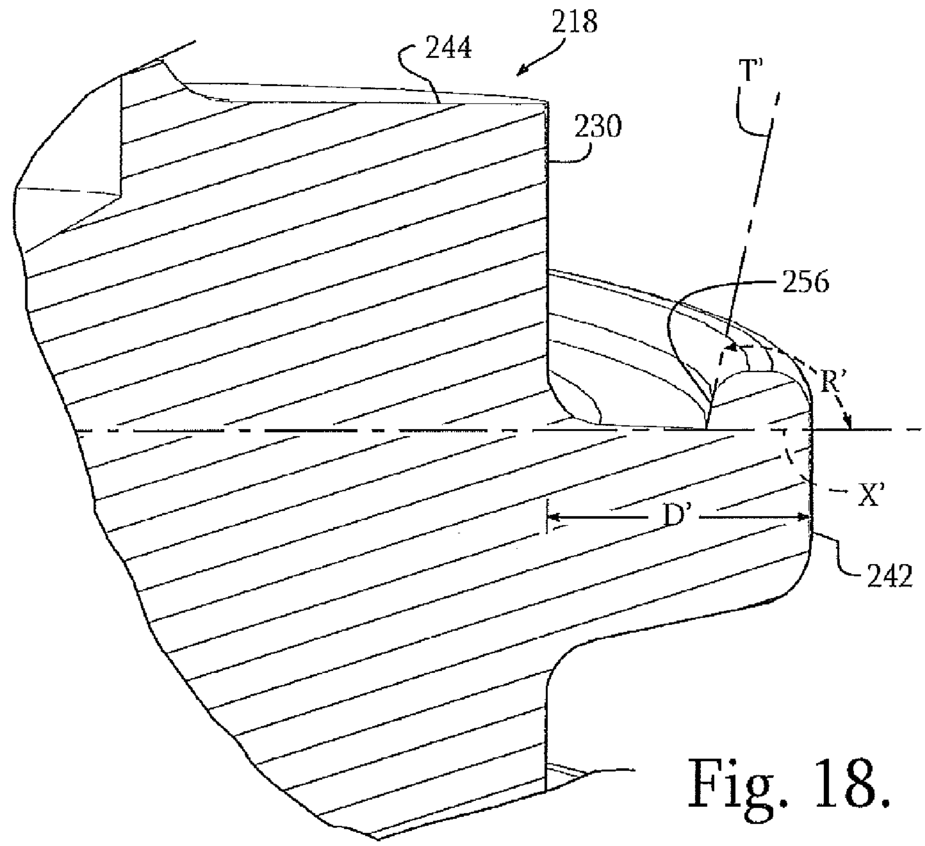
Fig. 18.

BONE ANCHOR RECEIVER UPRIGHT ARMS AND CLOSURES HAVING HELICALLY WOUND THREADS TO APPLY THRUST WITH CONTROLLED SPLAY

CROSS-REFERENCE TO RELATED APPLICATIONS

This application is a divisional of U.S. patent application Ser. No. 17/750,153, filed May 20, 2022, which is a continuation of U.S. patent application Ser. No. 16/905,621, filed Jun. 18, 2020, now abandoned, which is a continuation of U.S. patent application Ser. No. 16/391,049, filed Apr. 22, 2019, now U.S. Pat. No. 10,687,855, which is a continuation of U.S. patent application Ser. No. 15/689,080, filed Aug. 29, 2017, now U.S. Pat. No. 10,265,102, which is a continuation of U.S. patent application Ser. No. 14/567,217, filed Dec. 11, 2014, now U.S. Pat. No. 9,770,265, which is a continuation of U.S. patent application Ser. No. 14/086,728, filed Nov. 21, 2013, now U.S. Pat. No. 8,911,478, which claims the benefit of U.S. Provisional Application No. 61/851,300 filed Mar. 5, 2013 and U.S. Provisional Application No. 61/796,859 filed Nov. 21, 2012. Each of these applications is incorporated by reference in its entirety herein.

BACKGROUND OF THE INVENTION

The present invention is directed to structure for joining together parts of a medical implant, in particular for use with open bone anchors in spinal surgery, and in some embodiments thereof, for use with spinal bone anchors such as polyaxial screws.

Bone anchors, such as bone screws and hooks are utilized in many types of spinal surgery in order to secure various implants to vertebrae along the spinal column for the purpose of stabilizing and/or adjusting spinal alignment. For example, the most common mechanism for providing vertebral support is to implant bone screws into certain bones which then in turn support a longitudinal connecting member, such as a rod, or are supported by the connector. Although both closed-ended and open-ended bone anchors are known, open-ended anchors are particularly well suited for connections to longitudinal connecting members such as hard, soft or deformable rods, dynamic, soft or elastic connectors and connector sleeves or arms, because such rods or other connector members do not need to be passed through a closed bore, but rather can be laid or urged into an open channel within a receiver or head of such a bone anchor. Generally, the anchors must be inserted into the bone as an integral unit or a preassembled unit, in the form of a shank or hook and connected pivotal receiver. In some instances, a portion of such a preassembled unit, such as a shank of a polyaxial bone screw assembly, may be independently implanted into bone, followed by push- or pop-on assembly of a receiver portion of the unit that includes the open channel for receiving a rod or other longitudinal connecting member.

Typical open-ended bone screws include a threaded shank with a head or receiver having a pair of parallel projecting branches or arms which form a yoke with a U-shaped slot or channel to receive a portion of a rod or other longitudinal connecting member. Hooks and other types of connectors, as are used in spinal fixation techniques, may also include similar open ends for receiving rods or portions of other fixation and stabilization structure. After the rod or other longitudinal connecting member is placed in the receiver channel, a closure, typically in the form of a substantially cylindrical plug is often used to close the channel. Known closures include slide-on types, twist-on varieties that are rotated ninety degrees to a locked in position, and a variety of single start helically wound guide and advancement structures including, for example, thread forms having v-thread, reverse-angle, buttress or square thread forms, to name a few, as well as other non-threadlike helically wound forms.

It is known that the angled loading flank of a v-thread closure generates outward splay of spaced open implant receiver arms at all loading levels without limit. Thus, v-threaded closures or plugs are sometimes used in combination with outer threaded nuts that prevent outward splaying of the receiver arms. To overcome the splay problems of v-threaded closures, so-called “buttress” thread forms were developed. In a buttress thread, the trailing or thrust surface is linear and oriented somewhat downwardly in the direction of advancement with respect to the thread axis, while the leading or clearance surface is angled rearwardly in varying degrees, theoretically resulting in a neutral radial reaction of a threaded receptacle or receiver to torque on the threaded closure member being received thereby. In reverse angled thread forms, which theoretically positively draw the threads of a receptacle radially inwardly toward the thread axis when the reverse angle closure thread is torqued, provided the outer tip of the thread is crested and strong enough, the trailing linear surface of the external thread of the closure is angled toward the thread axis instead of away from the thread axis (as in conventional v-threads). Although buttress and reverse angle threads with linear loading surfaces reduce the tendency of bone screw receiver arms to splay outwardly, the arms may still be flexed outwardly by forces acting on the implant and the threads can be bent and deformed by forces exerted during installation. Closures made with square threads, again, having linear loading surfaces, theoretically keep all forces axially directed. However, it has been found that under a moderate load, square thread closures produce a marginal splay and under heavy load, splay can be considerable.

SUMMARY OF THE INVENTION

A closure structure embodiment according to the invention includes splay control surfaces for cooperating with a bone anchor for holding a spinal fixation longitudinal connecting member, such as a rod, the anchor having an open receiver with spaced apart arms defining a longitudinal connecting member receiving channel therebetween. Embodiments of the present invention provide balanced mating guide and advancement flange forms on both a closure and cooperating spaced apart arms of the bone anchor to control splay of the arms when the closure is rotated and advanced between the arms. Embodiments of the invention aid in splay control during torquing or tightening of the closure with respect to the arms that occurs when the closure abuts against an insert located in the receiver or directly against a longitudinal connecting member. In an illustrated embodiment, the closure flange form is located on an outer closure member and the closure includes an inner threaded set screw. A cooperating bone anchor assembly includes a compression insert located between the closure outer member and an upper portion of a bone screw shank that is located within a cavity of the receiver. Downward pressure by the outer closure member on the compression insert causes the insert to press downwardly on the bone screw shank upper portion that in turn presses against the receiver, locking the shank in a selected angular position with respect to the receiver. In the illustrated embodiment, the inner set screw eventually locks a rod or other longitudinal connecting member to the bone anchor. Although only a two piece closure is illustrated, one piece closures that press directly on a rod or other member are possible. Thus, more generally stated, closure embodiments of the invention are sized for being received within the receiver channel and adapted for rotation and advancement into the channel between the arms to capture a portion of the longitudinal connecting member in the channel and also control splay of the receiver arms during tightening of the closure with respect to other components of the assembly.

The closure guide and advancement flange form extends helically along the closure and about a central axis of the closure. A desired splay control is affected by certain parameters, including but not limited to flange form thickness, flange form height, height differentials along certain portions of the form, pitch, angular orientation of certain splay control contours and spacial relationships between the closure flange form and the receiver flange forms to result in axial loading on some portions of the forms and clearance and thus lack of loading on other portions of the forms.

The general shape of a “boot” can be used to describe certain closure flange form embodiments of the invention. The “boot” has a contoured or rounded “toe” pointing rearwardly and a “heel” facing downwardly. An upper most top surface of the “toe” remains unloaded in use.

More specifically, according to an aspect of the invention, the closure flange form includes a first portion located adjacent a root of the form and extending radially outwardly therefrom in a direction away from the central axis, the first portion having a first load flank surface. The closure flange form also has a second portion extending radially outwardly from a termination of the load flank to a crest of the flange form. The second portion includes a first splay control ramp and the contoured or rounded toe, the toe being spaced from the load flank both radially and axially. A radial distance defining a thickness of the first portion generally ranges between about forty percent to about sixty percent of an entire thickness of the closure flange form measured radially from the root to the crest, but can greatly vary. In certain preferred embodiments the flange form thickness of the first portion is about the same as a flange form thickness of the second portion.

An angle defined by a radius running from the closure central axis and perpendicular thereto with a substantial portion of the splay control ramp is oblique. In certain instances, when a majority of the splay control ramp is a radiused surface, such an angle may be defined by a tangent of such radiused surface, running from the load flank. Preferably, the angle ranges between about thirty-nine and about eighty-nine degrees.

A discontinuous receiver guide and advancement flange form extends helically about and along an inner surface of each receiver arm, the receiver flange form having a second load flank and a second splay control ramp engaging the first load flank and the first splay control ramp during mating of the closure flange form with the receiver flange form, the receiver flange form having clearance surfaces disposed in close spaced relation to a remainder of the closure flange form. Thus, each of the receiver arm flange forms are not identical in shape and size to the closure flange form or forms. Rather, a balance is created between the interlocking forms, both having a same or substantially similar cross-sectional area, and thus strength, to ensure engagement of the load flanks and splay control ramps of each of the forms.

The balanced interlocking forms also are shaped to ensure that the top surface of the toe portion of the closure flange form that is spaced from the root and extends axially upwardly is never loaded and thus the receiver flange forms are configured to provide space or clearance at not only stab flank or leading surfaces but also at the closure toe. Depending on initial engagement of mating splay control ramp surfaces, slopes can be controlled so that the closure flange form is able to draw in the upright arms of a receiver, which by comparison is typically the weaker of the flange form components.

Another aspect of the invention concerns the height of the closure flange form at certain locations. A closure guide and advancement flange form embodiment includes a crest portion with a first height measured axially (parallel to the closure central axis) and a root portion having a second axial height (measured parallel to the central axis), the first height measured from a top of an upwardly extending toe of the flange form to a stab flank and taken substantially along a crest surface of the flange form, the second height measured from a load flank of the flange form to the stab flank and taken substantially along a root surface of the flange form, the first height being one of slightly less and substantially equal to the second height.

The illustrated embodiment of a flange form according to the invention is a multi-start form, specifically a dual start form and thus two splay control forms are disposed on the closure structure, each having a start located near a bottom of the closure. It is foreseen that a single start flange form could be used in other embodiments of the invention. By way of explanation, it is noted that the force required to press a closure structure down onto a rod or other connector located between arms of an open implant is considerable. Even though a head or receiver portion of an open polyaxial bone anchor may be pivoted in a direction to make it easier for the arms of the open implant to receive a rod or other connector, spinal misalignments, irregularities and the placement of other surgical tools make it difficult to place the rod or other connector between the arms of the implant while a closure structure is mated with the open implant as well as used to push the rod or other connector downwardly into the implant. For example, when the closure is a cylindrical plug having a single start helically wound guide and advancement structure, such structure must be aligned with mating structure on one of the implant arms and then rotated until a portion of the structure is captured by mating guide and advancement structure on both arms of the implant, all the while the closure is being pressed down on the rod while other forces are pushing and pulling the rod back out of the implant. Integral or mono-axial open implants that cannot be pivoted to receive the rod are even more difficult to manipulate during the initial placement of the rod and initial mating rotation of a closure plug between the spaced, open arms of the implant. Therefore, extraordinary forces are placed on the implant and closure plug while the surgeon either pushes down on the rod or pulls up on the bone to get the rod in position between the implant arms and to initially push down upon the rod with the closure plug. The double starts of the illustrated closure provide for a more even and accurate pressing and rotation of the closure structure with respect to the receiver at the very beginning of the closure/receiver mating procedure, when alignment of the component parts is at its most difficult.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 17 is a front elevational view of an embodiment of an alternative splay control closure according to the invention with portions broken away to show the detail thereof.

FIG. 18 is an enlarged and partial front elevational view of the closure of FIG. 17 with portions broken away to show the detail thereof.

DETAILED DESCRIPTION OF THE INVENTION

Figure 1:
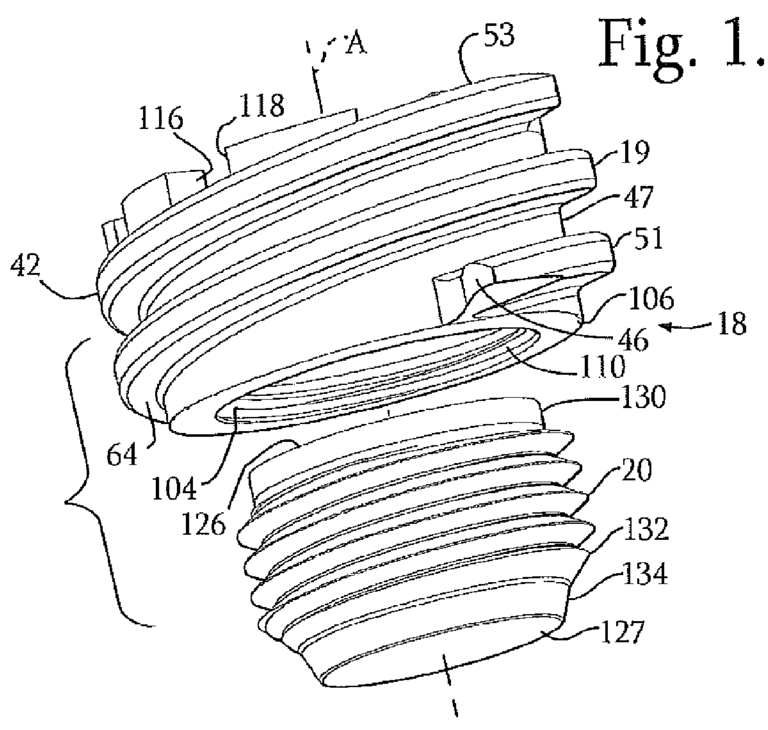
FIG. 1 is an exploded perspective view of a two piece closure according to an embodiment of the invention.

As required, detailed embodiments are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

It is noted that the helically wound splay control flange forms described in detail herein cannot be considered thread forms as flange forms include numerous features, including surfaces and contours, compound and non-linear, in addition to and not anticipated by traditional screw thread technology and nomenclature. However, certain terms used in this application will be similar to those used in thread form nomenclature. For example, in traditional v-thread nomenclature, a flank is often described as a thread face running from a root to a crest of a thread form with the root being the bottom surface joining flanks of two adjacent flanks and the crest being the top and bottom surfaces joining two flanks of a single thread form near an outer edge or tip thereof. In this application, the term flank may be used to describe certain surfaces of a flange form, such as a loading or thrust surface, but unlike a thread, a flange form flank does not necessarily connect a root to a crest of a particular form. Similarly, a crest or outermost edge surface of a flange form does not necessarily function as the surface that joins two flanks as other features, such as splay control surfaces and/or unloaded curves or contours, may be located between a flank and a crest. Furthermore, while a root surface of a flange form may typically be substantially cylindrical and a crest surface of a flange form may be at least partially cylindrical, such surface may also be sloped or curved. Thus, an entire outer surface which might be identified as a "crest" surface of a closure plug may or may not be at a uniform distance from a cooperating root surface.

Also, the terms lead, pitch and start, as such terms are used to describe other helically wound guide and advancement structures, are to be understood as follows: Lead is a distance along the axis of a closure or plug that is covered by one complete rotation (360 degrees) of the closure with respect to a mating structure. Pitch is the distance from a location on a crest or most outward surface of one flange form structure to the same location on the next or adjacent flange form. For example in a single-start thread-form, such as a single start, helically wound v-thread closure plug, lead and pitch are the same. Single start means that there is only one helically wound form wrapped around a cylindrical core, or in the case of embodiments of closures according to the present invention, wrapped around a cylindrical closure plug body and thus there is only one start structure or surface at a base or forward end of the closure body that initially engages a mating structure on an open implant. Each time a single start closure rotates one turn (360 degrees), the closure has advanced axially by a width of one helical flange form. Double-start means that there are two forms wrapped around a core body and thus there are two starting surfaces or structures on the closure plug. Therefore, each time a double-start body rotates one turn (360 degrees), such a body has advanced axially by a width of two helical flange forms. Multi-start means that there are at least two and may be up to three or more of such forms wrapped around a core body. Similar to threads, flange forms may also be coarse or fine. Course flange forms are those with a larger pitch (fewer forms per axial distance) and fine forms have a smaller pitch (more forms per axial distance).

Closures according to the invention may take a variety of forms, including single and multi-start options, one piece closures, two piece closures, closures with break-off heads, for example, and may be used with a wide variety of medical implants, including, but not limited to mono-axial screws and hooks, hinged or uni-planar screws and hooks and dual multi-piece polyaxial bone screws and hooks, as well as screws with sliding or pivoting inserts. A variety of polyaxial bone screws may also be used with splay control structures of the invention and the illustrated embodiment should not be considered limiting. For example, splay control structures of the invention may be used with bone screws having top loaded bone screw shanks with spherical heads (such as the illustrated bone screw 1) and also with bottom-loaded multi-part screw shanks as well as bottom loaded "pop-on" screws, such as Applicant's U.S. patent application Ser. No. 12/924,802, filed Oct. 5, 2010, for example, that is incorporated by reference herein. In this application, an embodiment of a two-piece, dual start closure, generally 18, according to the invention is shown in FIGS. 7-16, with an open implant in the form of a polyaxial bone screw apparatus or assembly, generally 1 that includes a shank 4, that further includes a body 6 integral with an upwardly extending substantially spherical upper portion or head 8; a receiver 10 having a cavity or inner chamber for receiving the shank head 8 communicating with an upper channel formed between opposed arms 11 having top surfaces 12; and a compression or pressure insert 14 having a lower surface 15 engaging the shank head 8 within the receiver cavity, the illustrated insert 14 also defining an inner channel between opposed upright arms 16, each having a top surface 17.

The illustrated closure 18 includes two pieces: an outer structure or fastener 19 having an outer guide and advancement structure in the form of a double-start helically wound splay control flange form and an inner thread sized and shaped for cooperation with a coaxial threaded inner plug 20, the helically wound forms of both of the structures 18 and 19 having an axis of rotation A. The closure top 18 is illustrated alone in FIGS. 1-6 and shown with the bone screw assembly 1 in FIGS. 7-16. In the closure illustrated in FIG. 1, the plug 20 is bottom or uploaded into the outer structure 19. However, it is foreseen that in other embodiments, the plug 20 may be down or top-loaded into the structure 19.

As will be described in greater detail below, the outer structure 19 of the closure top 18 mates under rotation with the receiver 10 having a central axis B with the axis A being aligned with the axis B, the structure 19 pressing downwardly against the insert 14 arm top surfaces 17, the insert surface 15 in turn pressing downwardly against the shank head 8 that in turn frictionally engages the receiver 10, locking the polyaxial mechanism of the bone anchor 1, (i.e., fixing the shank 4 at a particular angle with respect to the receiver 10). The closure inner plug 20 ultimately frictionally engages and presses against a longitudinal connecting member, for example, a rod 21, so as to capture, and fix the longitudinal connecting member 21 within the receiver 10 and thus fix the member 21 relative to a vertebra 23. The illustrated rod 21 is hard, stiff, non-elastic and cylindrical, having an outer cylindrical surface 22. However, a longitudinal connecting member for use with the assembly 1 may take the form of an elastic or deformable rod or have a different cross-sectional geometry. The longitudinal connecting member may also be a part of a soft or dynamic system that may include hard or soft structure for attaching to the assembly 1 and may further include a tensioned cord, elastic bumpers and spacers located between bone screws, for example. In the illustrated embodiment, the receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

Figures 6, 7, 8:
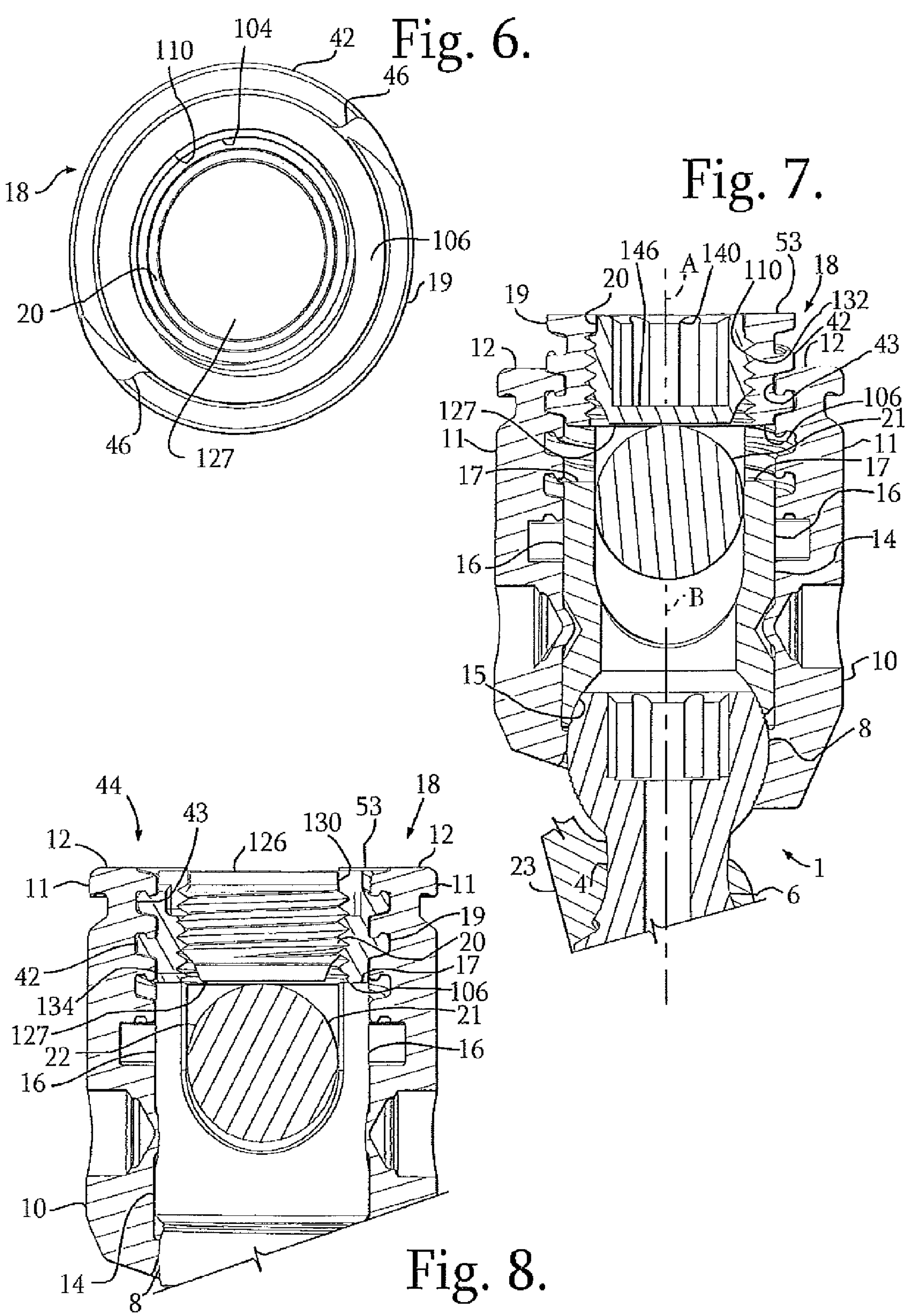
FIG. 6 is a reduced bottom plan view of the closure of FIG. 1.
FIG. 7 is a reduced front elevational view of the closure of FIG. 1, with portions broken away similar to FIG. 2 and shown in a first stage of mating engagement with an embodiment of a polyaxial bone screw having a shank, a receiver and a lower pressure insert and further shown with a rod, also shown in front elevation with portions broken away to show the detail thereof.
FIG. 8 is another front elevational view with portions broken away of the assembly shown in FIG. 7, the closure being shown in initial engagement with the lower pressure insert.

Returning to FIGS. 1-6, the illustrated multi-start closure 18 outer splay control structure 19 has a double or dual start helically wound guide and advancement structure in the form of a pair of identical helically wound forms 42, each illustrated as a flange form that operably joins with mating flange form structure 43 disposed on the arms 11 of the receiver 10 to result in an interlocking guide and advancement structure or arrangement, generally 44 (see FIGS. 7 and 8, for example). Although one particular flange form structure and relationship, generally 44, will be described herein with respect to the forms 42 and 43, it is noted that flange forms may be of a variety of geometries, including, for example, those described in Applicant's U.S. patent application Ser. No. 11/101,859 filed Apr. 8, 2005 (US Pub. No. 2005/0182410 published Aug. 18, 2005), which is incorporated by reference herein.

Each form 42 includes a start surface or structure 46 and thus, as shown in FIG. 6, the structure 19 includes two starts 46. Each of the forms 42 may be described more generically as being positioned as an inner flange of the overall structural arrangement 44 as each form 42 extends helically on an inner member that in the illustrated embodiment is the closure structure 19. The flange form 43, on the other hand, extends helically within an outer member that in the illustrated embodiment is in the form of the receiver 10 arms 11. The flanges 42 and 43 cooperate to helically guide the inner member or structure 19 into the outer member or receiver 10 when the inner member 19 is rotated and advanced into the arms 11 of the outer member 10. The inner and outer flanges 42 and 43 have respective splay regulating contours to control splay of the receiver arms 11 when the inner member 19 is strongly torqued therein. In some embodiments of the invention the member 19 may be a substantially solid plug that is eventually torqued against the rod 21 to clamp the rod within the receiver 10. In the illustrated embodiment, the inner threaded plug 20 is the feature that ultimately clamps down on the rod 21 and also mates with the member 19 via a v-thread that will be described in greater detail below.

Figure 2:
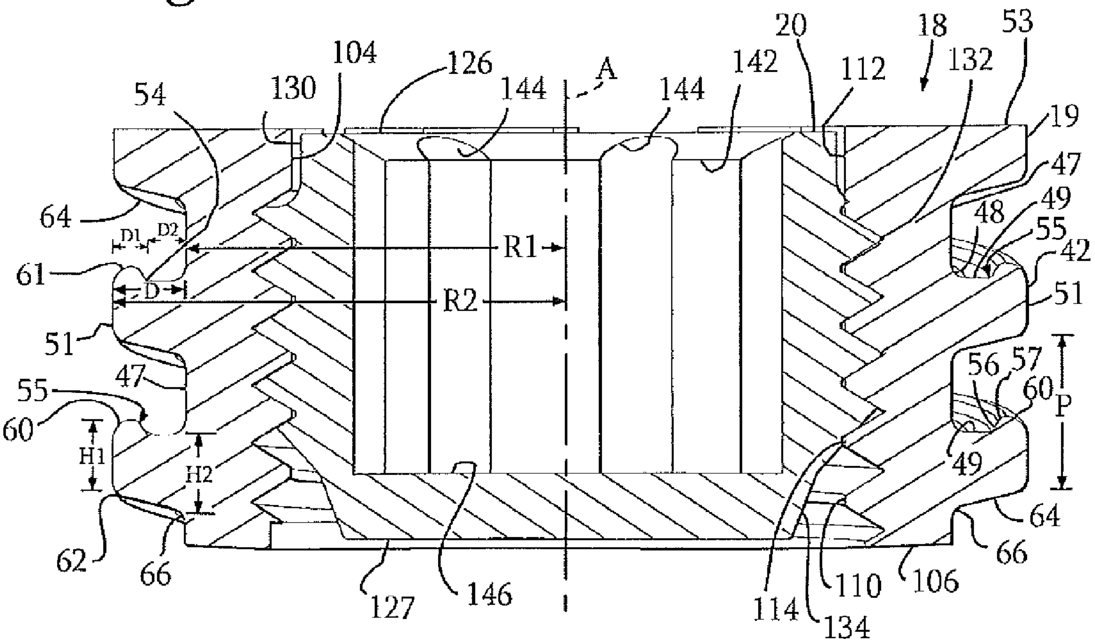
FIG. 2 is an enlarged front elevational view of the closure of FIG. 1 with portions broken away to show the detail thereof.
Figures 3, 4, 5:
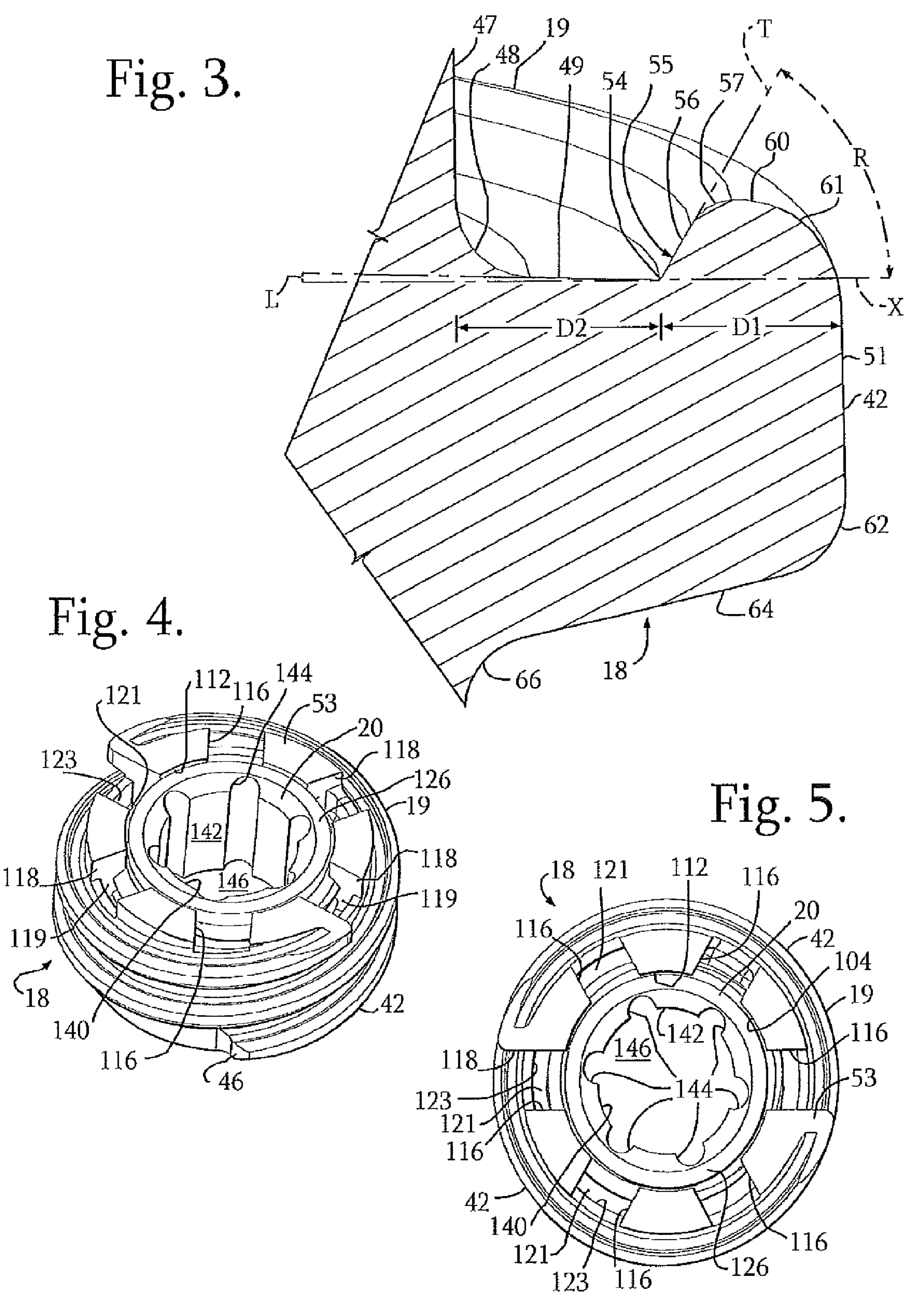
FIG. 3 is an enlarged and fragmentary view with portions broken away of the closure of FIG. 2.
FIG. 4 is a reduced perspective view of the closure of FIG. 1.
FIG. 5 is a reduced top plan view of the closure of FIG. 1.
Figure 15:
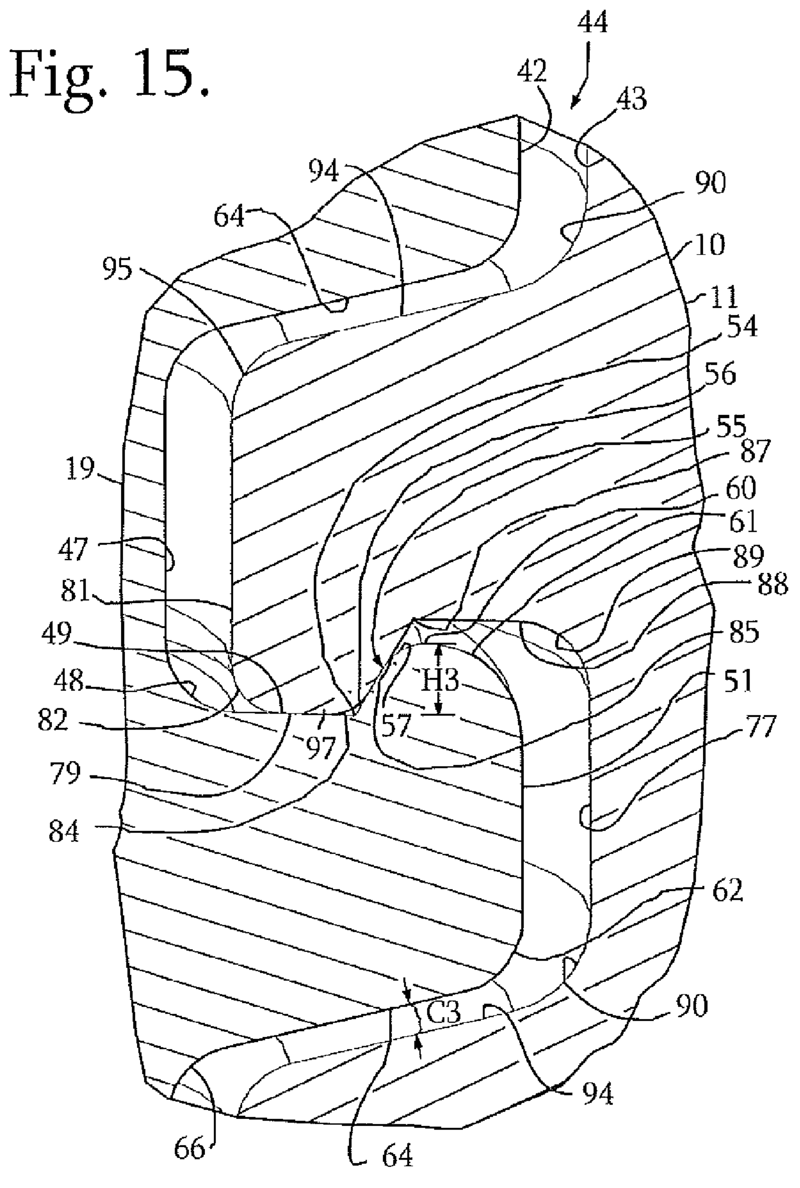
FIG. 15 is an enlarged and fragmentary front elevational view with portions broken away of the assembly of FIG. 14.

With particular reference to FIGS. 2, 3 and 15 each flange form 42 includes several surfaces or contours that helically wrap about the axis A. The contours of the flange form 42 include a root surface 47 that is helical and disposed substantially parallel to the axis A. A virtual cylinder formed by the root surface 47 has a radius R1 (radial distance between the axis A and the surface 47). Adjacent the root surface 47 is a radiused surface, curve or corner surface 48 that in turn is adjacent to a load or loading surface or flank 49. The load flank 49 is on a trailing side relative to a direction of advancement of the structure 19 along the axes A when the structure 19 rotatingly mates with the flange form 43 on the receiver arms 11. In the illustrated embodiment, in addition to sloping helically downwardly toward the start 46, the load flank 49 also slopes slightly downwardly in a direction running radially outwardly from the root surface 47 toward an outer or crest surface 51. However, the load flank 49 does not extend all of the way to the crest surface 51 as will be described in greater detail below. In some embodiments of the invention, the load flank 49, or at least portions thereof, may slope more steeply with respect to the horizontal, may be substantially horizontal (i.e., perpendicular to the axis A) or may even slope in a slightly upward direction toward a top surface 53 of the structure 19, i.e., reverse angle in nature. In the illustrated embodiment, the slightly downwardly sloping load flank 49 advantageously results in a thicker stronger flange form 42 structure at and near the root surface 47, giving the closure 19 a bigger bite of the cooperating form 43 than would be possible with a horizontal load flank. Although the downwardly sloping load flank 49 may actually cause an initial outward splay of the arms 11 during rotation of the form 42 into the form 43, the downward slope provides a remainder of the flange form 42 with additional clearance for drawing portions of the flange form 43 in a direction toward the structure 19 as will be described in greater detail below. The thickness or height of the form 42 near the root 47 also provides the form 42 with adequate strength for pulling the form 43 inwardly rather than relying solely on a bending moment created by a remainder of the form. With particular reference to FIG. 3, a preferred angle of slope (represented by the letter L) of the load flank 49 ranges between about one degree and about five degrees with respect to a radial line extending perpendicular to the axis A (illustrated as a horizontal dotted line X in FIG. 3), although other angles are possible.

With further reference to FIGS. 2 and 3, in certain embodiments, as is shown in the present illustration, a substantial portion of the crest surface 51 is substantially parallel to the root surface 47. Thus, a virtual cylinder formed by the crest surface 51 has a radius R2 (radial distance between the axis A and the surface 51). However, in other embodiments, the outer or crest surface may include radiused surfaces at a top and bottom thereof and may further have other sloping portions that are not parallel to the root surface. Thus, although the radial measurements R1 and R2 are substantially uniform for the illustrated embodiment, it is noted that in other embodiments, R1 would refer to the smallest distance from the axis A to a root surface or point 47 and R2 would refer to the greatest distance between the axis A and a crest surface or point. With further reference to FIG. 2, a distance D identifies a depth of the flange form 42 from the crest 61 to the root 47. Stated in another way, D=R2−R1. The distance or depth D may be further broken down into D1 and D2 wherein D1 is a distance from the crest surface 51 to the load flank 49 and D2 is a length of the load flank 40 measured from the root surface 47 a location 54 where the load flank 49 terminates. The distance D1 can be equal to, less than or greater than D2. The distance or depth D2 may preferably range from between about forty to about sixty percent of the total distance D. In a preferred embodiment of the invention D1 is slightly less than or substantially equal to D2, with the total D preferably ranging between about 0.65 mm and about 1.1 mm (between about 0.026 in. and about 0.043 in.). A most preferred value for D ranges between about 0.70 mm and about 0.90 mm (between about 0.028 in. and about 0.035 in.). However, flange depths or lengths D can range from about 0.2 to over 2.0 mm.

With particular reference to FIG. 3, adjacent the loading flank 49 at the location 54 and running upwardly (in a direction toward the top surface 53) as well as outwardly toward the crest surface 51, is a splay control ramp or surface portion, generally 55 that in the illustrated embodiment includes a lower substantially frusto-conical surface 56 and an upper convex radiused surface portion 57. It is noted that although the splay control ramp 55 is ultimately an "anti-splay" structure for interlocking with the flange form 43 on the receiver arms 11, prohibiting undesirable outward splay of the arms 11 when in full locking engagement with the closure structure 19, it has been found that during torquing of the closure structure 19 with respect to the receiver arms 11, the flange form 42, and depending on geometry, even a portion of the ramp 55 may cause an outward splay in one or more surrounding components, so the term "splay control" is being used herein rather than the term "anti-splay" for the various flange form components and contours. It is also noted that in other embodiments of the invention, the splay control ramp may include additional contours or curves that may control splay either inwardly or outwardly. The loading flank surfaces that include the load flank 49 and the splay control ramp 55 are typically non-linear and compound in surface contour, the ramp 55 providing splay control. In the illustrated embodiment, the radiused surface 57 is adjacent to another radiused surface 60 that curves outwardly and then downwardly, converging into the crest surface 51. The flange form can be thought of as a "boot," having a toe 61 and a heel 62. The splay control ramp surfaces 56 and 57 and the upper rounded or radiused surface 60 define the protrusion, bead or toe 61 of the flange form 42 that is directed generally upwardly toward the top surface 53 and also outwardly away from the loading flank 49 and a downward or leading facing heel 62. As will be described in greater detail below with respect to the cooperating flange form 43 on the receiver arms 11, the surfaces defining the toe 61 are spaced from the load flank 49, and, unlike the load flank 49, the toe 61 is never loaded, but always spaced from the flange form 43 of the receiver 10. In the illustrated embodiment, the individual surfaces that lead up to the toe and make up the toe are gradually increasing in radius. In other words, the surface 60 has a radius that is greater than a radius of the surface 57 and the surface 61 has a radius greater than the radius of the surface 60. The illustrated heal 62 is also radiused and forms a lower corner of the flange form, the heal 62 being located adjacent the crest surface 51 at a base thereof and joining the crest surface 51 with a stab surface or flank 64. The stab flank 64 is located generally opposite the load flank 49 and the toe 61. The load flank 49 may also be referred to as a thrust surface while the stab flank 64 may also be referred to as a clearance surface. To complete the illustrated flange form 42 geometry, a curved surface 66 made up of one or more radiused surface portions joins the stab surface 64 to the root surface 47.

With further reference to FIG. 2, and as described previously herein, a pitch P is a distance from a point on the crest surface 51 of one flange form to a corresponding point on the crest surface 51 of an adjacent form, the distance being measured parallel to the axis A. In the illustrated embodiment of a two-start flange form, the distance P is measured between two forms having different starts. It has been found that the smaller or finer the pitch, the greater the thrust for a given torque. Typically, for polyaxial mechanisms utilizing the flange form 42, torques range between about 75 and about 125 inch pounds (between about 8.5 and about 14.1 Newton-meters (Nm)). To perform well in such a torque range, flange forms of the invention may vary more widely in pitch, for example, the pitch P may range from about 0.040 inches to about 0.120 inches, with a pitch P range of about 0.060 inches to about 0.070 inches being preferred in embodiments having single start flanges and higher pitches in embodiments having dual start flanges.

Another measurement illustrated in FIG. 2 is a first height H1 that runs from an upper most point of the surface 60 defining the toe 61 (upper being in a direction toward the top surface 53) to an opposite or lower most point of the curve or corner 62, measured parallel to the axis A. Another measurement is a second height H2 that is a distance from the load flank 49 the curved surface 66 that joins the stab flank 64 with the root surface 47. The measurements H1 and H2 provides a sense of balance of the flange form 42 at either side of the load flank 49, with H1 preferably being slightly less than or equal to H2. As indicated above, a downward slope of the load flank 49 results in an H2 value of the flange form 42 near the root 47 that advantageously resulted in a stronger form for controlling splay than, for example, an embodiment wherein the flank 49 is horizontal (perpendicular to the axis A).

Returning to the splay control ramp 55, as illustrated in FIG. 3, the lower ramp surface 56 is shown extended (the dotted line T) and an angle R is formed by the dotted line T and a line X disposed perpendicular to the closure axis A. In the illustrated embodiment, the angle R is approximately sixty degrees. Preferably, the splay control ramp angle R is less than ninety degrees, and more preferably ranges between about thirty and about eighty-nine degrees and even more preferably between about fifty-five and about eighty-five degrees. Most preferred are splay control ramps with the angle R ranging between about seventy and about eighty degrees. Stronger splay control ramps are over seventy degrees and weaker ramps are less than seventy degrees. As described above, in some embodiments, rather than being defined primarily by a frusto-conical surface, the splay control ramp 55 may be made up of one or more radiused surfaces. In such embodiments, the dotted line T represents a tangent line originating at the load flank 49 and intersecting a contoured surface or surfaces defining a substantial portion of the splay control ramp 55.

Figures 9, 10, 11, 12, 13:
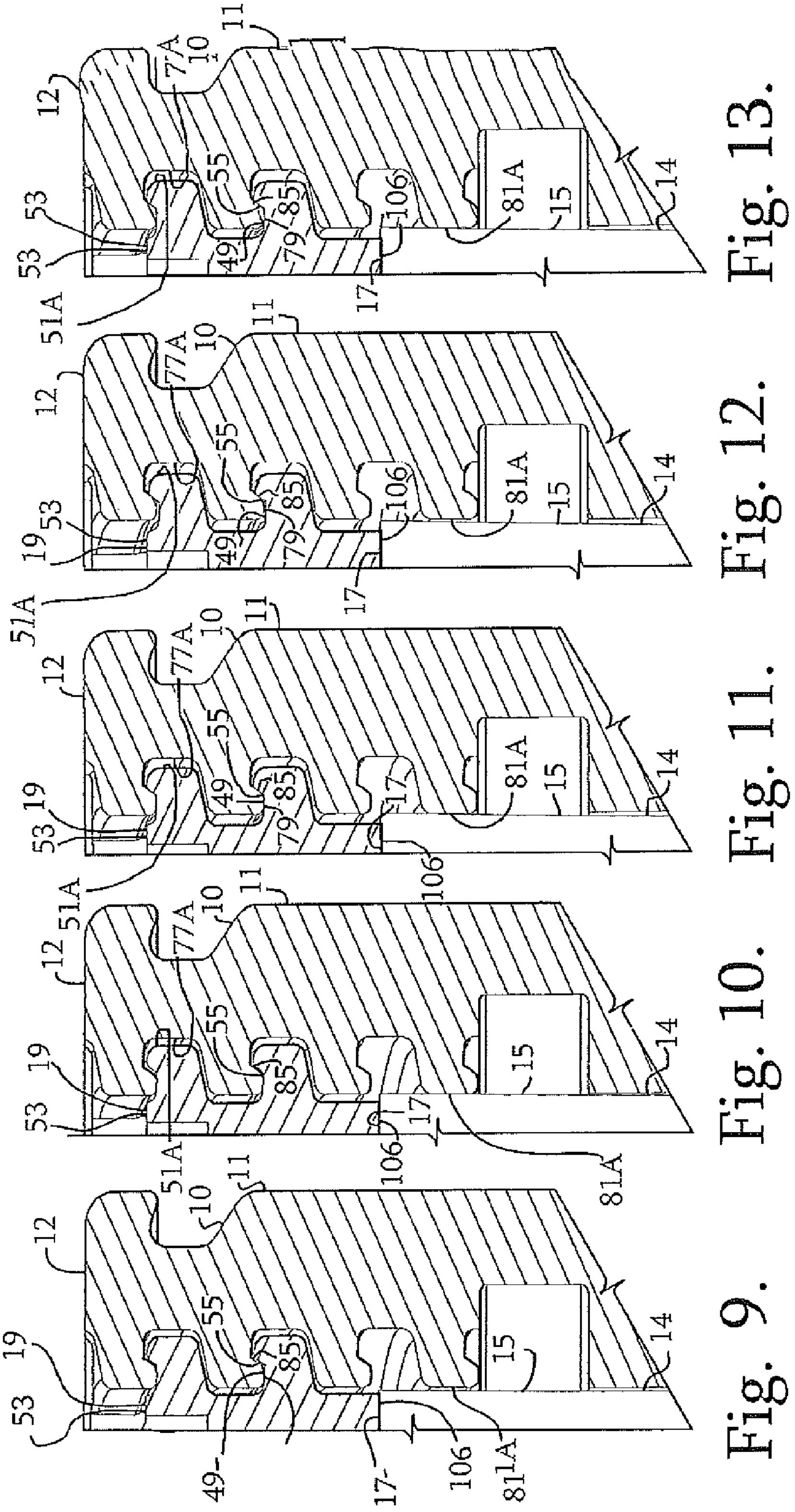
FIG. 9 is an enlarged and partial front elevational view with portions broken away of the assembly shown in FIG. 8, illustrating contact between the closure top outer portion and the insert, but no loading.
FIG. 10 is a partial front elevational view with portions broken away of the assembly as shown in FIG. 9, but illustrating a light load being placed on the insert by rotation of the closure top outer portion downwardly against the insert.
FIG. 11 is a partial front elevational view with portions broken away of the assembly as shown in FIG. 10, but illustrating a medium load being placed on the insert by further rotation and downward movement of the closure top outer portion.
FIG. 12 is a partial front elevational view with portions broken away of the assembly as shown in FIG. 11, but with a high load being placed on the insert by further rotation and downward movement of the closure top outer portion.
FIG. 13 is a partial front elevational view with portions broken away of the assembly as shown in FIG. 12, but with a higher load sufficient to frictionally fix the insert against the shank head and thus the shank head against the receiver.
Figures 14, 16:
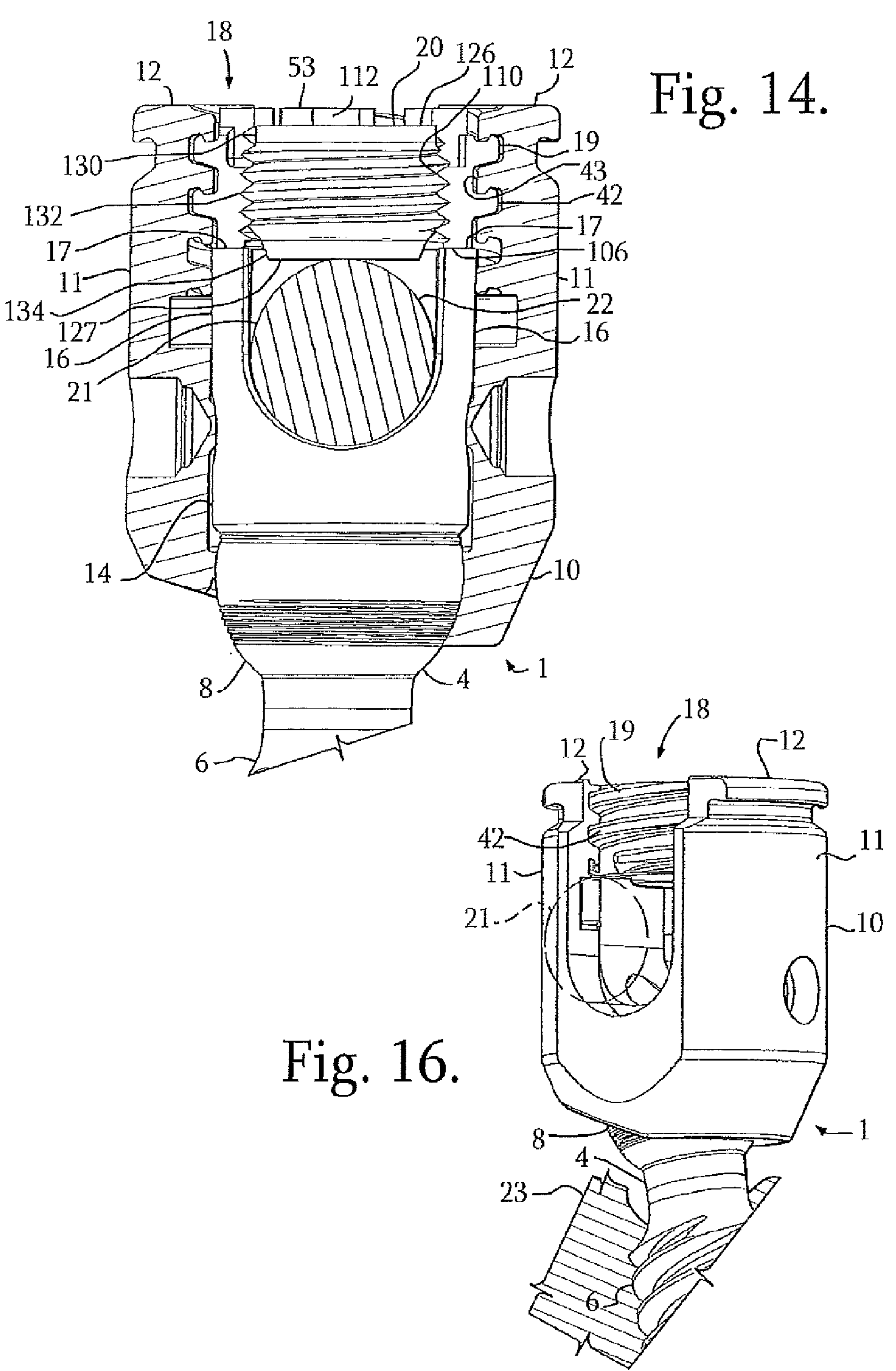
FIG. 14 is a reduced and partial front elevational view with portions broken away of the assembly of FIG. 13 and further showing the closure inner set screw rotated and lowered into fixed, frictional engagement with the rod.
FIG. 16 is a reduced and partial perspective view of an assembly similar to that shown in FIG. 14, differing from the assembly of FIG. 14 only in that the shank is positioned at an angle with respect to the receiver, the rod being shown in phantom.

With particular reference to FIGS. 13-15, the flange form 43 located on each receiver arm 11 cooperates with the form 42, but is not identical thereto or even a mirror image thereof. Rather, a balance is created between the flange form 42 and the flange form 43 to provide load and clearance surfaces to result in a desired splay control of the receiver arms 11. Stated in another way, many cross-sectional shapes of the form 43 are nearly the same as adjacent cooperating shapes of the form 42, thus, the forms are substantially balanced in cross-sectional area, but clearances between certain surfaces are important, for example, the form 43 must always be spaced from surfaces making up the unloaded toe 61, and engagement by other surfaces is important, for example, the form 43 must engage, touch or slide upon, the form load flank 49 and splay control ramp 55. Finally, to minimize stress risers, corners of the two flange forms 42 and 43 must be radiused.

With specific reference to FIG. 15, the flange form 43 includes a load flank 79 and a crest surface 81. A radiused corner surface 82 connects the flank 79 and the crest surface 81. At an opposite side of the load flank 79 a radiused surface 84 joins the flank 79 with a splay control ramp 85. The splay control ramp 85 terminates at a location 87 that is adjacent a clearance surface 88 that extends inwardly toward the root surface 77. Another radiused surface 89 connects the clearance surface 88 with the root surface 77. At an opposite side of the root surface 77, another radiused corner surface 90 connects the root surface 77 with a stab flank or surface 94. To complete the geometry of the flange form 43, a radiused corner surface 95 connects the stab flank 94 with the crest surface 81. In FIG. 15, the flange form 43 load flank 79 is shown frictionally engaging the closure form 42 load flank 49. Unlike the closure form 42 that does not engage the form 43 and thus is never loaded, the load flank 79 located on the receiver arms 11 primarily defines an engaged, loaded toe 97 of the form 43. Thus, although the flange form 42 looks very much like the flange form 43, similar geometric forms do not perform similarly. As is also shown in FIG. 15, the splay control ramp 85 of the flange form 43 engages the splay control ramp 55 of the flange form 42 when the closure structure 19 is mated and torqued into tight locking engagement with the form 43 on the receiver arms 11. A step-by-step observance of the cooperation between the forms 42 and 43 during mating engagement will be described below with respect to FIGS. 9-13. The root surface 77 of the form 43 is always spaced from the crest surface 51 of the form 42 and the crest surface 81 of the form 43 is always spaced from the root surface 47 of the form 42 during rotation and locking of the closure structure 19 with respect to the receiver arms 11. As stated previously, the toe 61 of the closure flange form 42 is always unloaded, thus the splay control ramp 85 of the flange form 43 is sized such that the termination location 87 of the ramp 85 is always spaced from the form 42 toe surfaces 57 and 60. Likewise, the clearance surface 88 and corner surface 89 of the form 43 are sized and contoured to clear the form 42 toe surface 60 as well as the crest surface 51. In the illustrated embodiment, with reference to FIG. 15, a height H3 of the toe portion of the closure flange form measured from the termination 54 of the flank surface 49 to a top of the surface 60 is greater than a clearance C3 measured between the closure stab surface 64 and the receiver stab flank 94.

In general, the load flanks 49 and 79 are positively engaged and axially loaded, that is, loaded in the direction of the axis A, when the closure member 19 is advanced into the receiver arms 11. As relative torque between the inner closure member 19 and the outer member arms 11 increases, by engagement with the insert 14 of the illustrated embodiment, for example, and in other embodiments by engagement with a clamped member such as the rod 21, there is a tendency for the arms 11, to splay outwardly away from the axis A. At such time, the splay control ramps 55 and 85 mutually engage in a radial direction to interconnect and mechanically lock, resisting the splay tendency of the receiver arms 11. Thus, relative torque between the inner and outer members 19 and 11 can be much higher in comparison to conventional V-threads or guide and advancement structures which do not have splay control contours, thereby allowing a considerably higher, more positive clamping force to be applied to the closure 19 and ultimately to the rod 21 by the inner set screw 20 as will be described in greater detail below.

Prior to describing the use of the closure 18 with respect to the bone anchor 1 as shown in FIGS. 7-16, other features of the closure 18 shown in FIGS. 1-6 shall be described. With particular reference to FIG. 1, an exploded view of the nested closure structure or closure top 18 that includes the outer fastener structure 19 and the uploaded inner set screw 20 is shown. It is noted that anti-splay structure of the invention may also be utilized on single-piece cylindrical plug-like closures as well as on other types of one and two piece nested closures, for example, those having a break-off head that separates from the closure when installation torque exceeds a selected level, such as the closures disclosed in Applicant's U.S. Pat. No. 7,967,850 (see, e.g., FIGS. 22-25 and accompanying disclosure), that is incorporated by reference herein. The illustrated fastener stricture 19 further includes a through-bore 104 extending along the axis A and running completely through the fastener 18 from the top surface 53 to a bottom surface 106. The bottom surface 106 is substantially planar and annular and configured for being received between the receiver arms 11 and for exclusively abutting against the substantially planar top surfaces 17 of the insert arms 16, the insert 14 arms 16 being configured to extend above the rod 21 such that the closure surface 106 is always spaced from the rod 21 or other longitudinal connecting member portion received by the insert arms 16 and located within the receiver 10.

As indicated previously, the closure or fastener structure 19 is substantially cylindrical and the two flange forms 42 project substantially radially outwardly. The closure structure 18 helically wound flange form 42 start structures 46 are located on opposite sides of the closure structure and are both located adjacent the bottom surface 106. When the closure structure 19 is rotated into the receiver 10 between receiver arms 11, each having the flange form 43 guide and advancement structure, the start 46 engages mating guide and advancement structure 43 on one arm 11 and the opposite start 46 simultaneously engages guide and advancement structure flange form 43 on the opposing arm 11, both forms 42 being simultaneously captured by the mating forms 43 on the opposed arms 11. As the structure 19 is rotated, the structure advances axially downwardly between the arms 11 and presses evenly down upon the insert 14 arm top surfaces 17. Each time the illustrated duel- or double-start closure plug 19 is rotated one complete turn or pass (three hundred sixty degrees) between the implant arms, the closure 19 advances axially into the receiver 10 and toward the insert 14 by a width of two helical flange forms. The closure 19 is sized for at least one complete rotation (three hundred sixty degree) of the closure 19 with respect to the receiver 10 open arms 11 to substantially receive the closure 18 between the implant arms. Multi-start closures of the invention may have two or more coarse or fine helical forms, resulting in fewer or greater forms per axial distance spiraling about the closure plug body and thus resulting in plugs that rotate less or more than one complete rotation to be fully received between the implant arms. Preferably, helically wound forms of the multi-start closure of the invention are sized so as to spiral around a cylindrical plug body thereof to an extent that the closure rotates at least ninety-one degrees to fully or substantially receive the closure 19 between the arms of the bone screw receiver or other open implant. Particularly preferred guide and advancement structures are sized for at least one complete turn or pass (three-hundred sixty degree) of the closure between the receiver 10 arms 11 and as many as two to three rotations to be fully received between implant arms.

Returning to FIGS. 1 and 2, at the closure structure base or bottom surface 106 and running to near the top surface 53, the bore 104 is substantially defined by a guide and advancement structure shown in the drawing figures as an internal V-shaped thread 110. The thread 110 is sized and shaped to receive the threaded set screw 20 therein as will be discussed in more detail below. Although a traditional V-shaped thread 110 is shown, it is foreseen that other types of helical guide and advancement structures may be used. Adjacent the closure top surface 53, the bore 104 is defined by a cylindrical surface 112 that runs from the top surface 53 to the v-thread 110. The cylindrical surface has a radius measured from the axis A that is the same or substantially similar to a radius from the axis A to a crest 114 the v-thread 110. In the illustrated embodiment, a distance from the top surface 53 to the v-thread 110 measured along the surface 112 is greater than a pitch of the v-thread, the surface 112 acting as a stop for the inner set screw or plug 20, preventing the screw 20 from rotating upwardly and out of the structure 19 at the top surface 53. However, it is foreseen that the surface 112 may be taller or shorter than shown, and that in some embodiments, a radially inwardly extending overhang or shoulder may be located adjacent the top surface 53 to act as a stop for the set screw 20. In other embodiments, the set screw 20 may be equipped with an outwardly extending abutment feature near a base thereof, with complimentary alterations made in the fastener 19, such that the set screw 20 would be prohibited from advancing upwardly out of the top of the structure 19 due to abutment of such outwardly extending feature of the set screw against a surface of the fastener 19. In other embodiments, the central set screw may be rotated or screwed completely through the outer ring member.

With particular reference to FIGS. 4 and 5, formed in the top surface 53 of the fastener 19 is a cross-slotted internal drive, made up of three spaced cross-slots, or stated in other way, six equally spaced radial slots 116. An upper portion 118 of each slot 116 extends from the bore 104 radially outwardly to the flange form 42 root surface 47 and thus completely through the top surface 53 of the structure 19, each upper portion 118 being adjacent the cylindrical surface 112 along an entire height thereof. Another, lower portion 119 of each slot 116 extends downwardly below the cylindrical surface 112 and cuts into the v-thread 110, terminating at a substantially planar base surface 121 and being partially defined by a cylindrical wall 123. The cross-slotted drive slots or grooves 116 are advantageous in torque sensitive applications: the more slots, the greater the torque sensitivity. Further, the slot lower portions 119 provide additional surfaces 121 and 123 for gripping by a cooperating drive tool (not shown) sized and shaped to be received by the slot lower portions 119.

The up-loadable set screw 20 has a substantially annular and planar top 126 and a substantially circular planar bottom 127. The screw 20 is substantially cylindrical in shape and coaxial with the fastener 18. The screw 20 is substantially cylindrical and includes an upper outer cylindrical surface 130 adjacent a v-thread surface portion 132 that in turn is adjacent to a lower frusto-conical surface 134 that runs to the base or bottom surface 127. The cylindrical surface 130 is sized and shaped to be received by the inner cylindrical surface 112 of the outer fastener 19. The v-thread 132 is sized and shaped to be received by and mated with the inner thread 110 of the fastener 19 in a nested, coaxial relationship. The frusto-conical surface 134 is sized and shaped to clear the insert 14 arms 16 are exclusively press upon the rod 21 as shown, for example, in FIG. 14.

As illustrated, for example, in FIGS. 2 and 5, the set screw 20 includes a central aperture or internal drive feature 140 formed in the top 126 and sized and shaped for a positive, non-slip engagement by a set screw installment and removal tool (not shown) that may be inserted through the bore 104 of the fastener 19 and then into the drive aperture 140. The drive aperture 140 is a poly drive, specifically, having a hexa-lobular geometry formed by a substantially cylindrical wall 142 communicating with equally spaced radially outwardly extending (from the axis A) rounded cutouts or lobes 144. The wall 142 and the lobes 144 terminate at a substantially planar driving tool seating surface 146. Although the hexa-lobular drive feature 140 is preferred for torque sensitive applications as the lobes are able to receive increased torque transfer as compared to other drive systems, it is noted that other drive systems may be used, for example, a simple hex drive, star-shaped drive or other internal drives such as slotted, tri-wing, spanner, two or more apertures of various shapes, and the like. With particular reference to FIGS. 1 and 2, the central set screw aperture 140 cooperates with the central internal bore 104 of the fastener 19 for accessing and uploading the set screw 20 into the fastener 19 prior to engagement with the bone screw receiver 10. After the closure structure 19 is inserted and rotated into the flange form 43 of the bone screw receiver 10, the set screw 20 is rotated by a tool engaging the drive feature 140 to place the set screw bottom 127 into frictional engagement with the rod 21 or other longitudinal connecting member. Such frictional engagement is therefore readily controllable by a surgeon so that the rod 21 may be readily manipulated until late in the surgery, if desired. Thus, at any desired time, the set screw 20 may be rotated to drive the screw 20 into fixed frictional engagement with the rod 21 without varying the angular relationship between the receiver 10 and the bone screw shank 4.

It is foreseen that the set screw 20 may further include a cannulation through bore extending along a central axis thereof for providing a passage through the closure 18 interior for a length of wire (not shown) inserted therein to provide a guide for insertion of the closure top into the receiver arms 11. The base 27 of the screw 20 may further include a rim for engagement and penetration into the surface 22 of the rod 21 in certain embodiments of the invention.

When the closure 18 is used with a bone anchor 1 as shown in the drawing figures, preferably, the receiver 10 and the compression insert 14 of the bone screw 1 are assembled at a factory setting that includes tooling for holding, alignment and manipulation of the component pieces, as well as crimping a portion of the receiver 10 toward the insert 14. In the illustrated embodiment, the shank 4 is also assembled with the receiver 10 and the insert 14 at the factory. In other bone screw embodiments, for example when the bone screw shank is a bottom loaded "pop-on" screw, such as described, for example, in applicant's U.S. patent application Ser. No. 12/924,802 that has already been incorporated by reference herein, it may be desirable to first implant the shank, followed by addition of a pre-assembled receiver and compression insert (and other components, such as a retaining ring) at the insertion point. In this way, the surgeon may advantageously and more easily implant and manipulate the shanks, distract or compress the vertebrae with the shanks and work around the shank upper portions or heads without the cooperating receivers being in the way. In other instances, including non-pop-on top loaded bone screw shank embodiments, it may be desirable for the surgical staff to pre-assemble a shank of a desired size and/or variety (e.g., surface treatment or roughening the shank upper portion and/or hydroxyapatite on the shank body), with the receiver and compression insert. Allowing the surgeon to choose the appropriately sized or treated shank advantageously reduces inventory requirements, thus reducing overall cost.

As illustrated in FIG. 7, the entire assembly 1 made up of the assembled shank 4, receiver 10 and compression insert 14, is screwed into a bone, such as the vertebra 23, by rotation of the shank 4 using a suitable driving tool (not shown) that operably drives and rotates the shank body 6 by engagement thereof at an internal drive thereof. Specifically, the vertebra 23 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the assembly 1 is threaded onto the guide wire utilizing a cannulation bore of the shank 4. The shank 4 is then driven into the vertebra 23 using the wire as a placement guide. It is foreseen that the shank and other bone screw assembly parts, the rod 21 (also having a central lumen in some embodiments) and a variation of the closure top 18 having a central through bore could be inserted in a percutaneous or minimally invasive surgical manner, utilizing guide wires.

Again, with reference to FIG. 7, the rod 21 is eventually positioned in an open or percutaneous manner in cooperation with the at least two bone screw assemblies 1. The closure structure 18 made up of the outer fastener 19 and the inner set screw 20 (already mated with the fastener thread 110) is then inserted into the receiver arms 11 at the top 12 thereof and the fastener is advanced by rotation between the arms 11 of each of the receivers 10 at the flange form two starts 46 as previously described herein.

With reference to FIGS. 8 and 9, the closure structure 19 is rotated, using a tool engaged with the drive slots 116 until the structure 19 bottom surface 17 engages the insert arm top surfaces 17. Then, with reference to FIGS. 10-13, the structure 19 is rotated until a selected torque is reached. For example, about 80 to about 120 inch pounds of torque on the closure structure 19 may be applied for fixing the insert 14 against the bone screw head 8 that in turn fixes the head 8 with respect to the receiver 10.

With particular reference to FIGS. 9-13, FIG. 9 is an enlarged and partial view of the assembly as shown in FIG. 8, showing the closure 19 rotated to an initial position wherein the closure bottom surface 17 is engaging the insert arms 16 at the top surfaces 17 thereof, but not otherwise pressing downwardly on the insert 14. Thus, there is minimal or almost zero pressure or load in the axial direction (with reference to the axis A) between the load flank 49 of the dual closure forms 42 on the fastener 19 and the load flank 79 of the receiver forms 43 located on each arm 11.

Furthermore, as can be seen in FIG. 9, there is a gap between the splay control ramps 55 of the forms 42 of the closure 19 and the splay control ramps 85 of the forms 43.

With reference to FIG. 10, further rotation of the fastener 19 with respect to the receiver arms 11 that produces a light load on the flanks 49 and 79, results in some splay of the insert 14 as indicated by the initial gap between the insert arm 16 and the flange form 43 crest surface 81 indicated by the reference numeral 81A located below the fastener 19 in FIG. 9 as compared to the insert arm 16 touching the crest surface at the location 81A in FIG. 10.

When a medium load is placed on the form 43 by further rotation of the form 42 as shown in FIG. 11, the receiver arms 11 begin to splay outwardly. This is evident, for example, by looking at a space between the flange form 42 crest surface 51 at a location 51A and the flange form 43 root surface 77 at a location 77A in FIG. 10 as compared to a wider space between the forms at the locations 51A and 77A in FIG. 11.

As the load increases further as shown in FIG. 12, the outward splaying of the receiver arms 11 increases slightly and the load flanks 79 of the arm flange forms 43 raise up off of the load flanks 49 of the closure 19. The rotation of the fastener flange forms 42 with respect to the arm flange forms 43 causes an upward and outward sliding movement of the splay control ramp 85 along the splay control ramps 55.

With reference to FIGS. 13 and 15, final tightening and torque between the flange forms 42 and 43 causes the flange form 42 to pull inwardly on the flange form 43, reducing the outward splay and resulting in fully engaged loading flanks 55 and 85. Any further outward splay of the arms 16 of the insert 14 is also prohibited by the receiver arms 11 that now press inwardly on the insert 14 as evidenced by the lack of gap between the insert arm 16 and the flange form 43 crest surface 81 at the location 81A as compared to th slight gap shown at the location 81A in FIG. 12. As is shown in FIGS. 9-13, during tightening of the closure structure 19 into the receiver arms 11, there is a push/pull relationship between the closure 19 flange forms 42 and the receiver forms 43. Initially, the closure 19 body and the flange form structure defined by the slightly downwardly sloping load flank 49, push outwardly on the receiver arms 11. However, as the form 42 is rotated within a cooperating form 43, the initial expansion or splay of the arms 11 provides surfaces and contours for the control ramp surfaces 55 to grip and draw back in a direction toward the axis A. It is noted that throughout the tightening, torquing process, the toe 61 of the flange form 42 is never loaded and always spaced from surfaces of the flange form 43.

With reference to FIG. 14, the inner set screw 20 is then rotated, using a tool engaged with the drive feature 140 until the set screw bottom surface 127 presses the rod 21 into full frictional engagement with the insert 14. As shown in FIG. 14, during tightening of the set screw 20 against the rod surface 22, there is no measurable outward splay of the receiver arms 11 as the flange forms 42 of the outer fastener 19 are in gripping interlocking engagement with the flange forms 43 on the receiver arms. If adjustment of the rod 21 is desired, the inner set screw 20 may be rotated in an opposite direction, loosening the rod 21, but not the locked polyaxial mechanism created by the outer fastener 19 pressing downwardly upon the insert 14 that in turn locks the bone screw shank 4 with respect to the receiver 10. If, however, removal of the rod is necessary, disassembly is accomplished by using the driving tool (not shown) that mates with the internal drive slots 116 on the closure structure 19 to rotate and remove such closure structure from the cooperating receiver 10. Disassembly is then accomplished in reverse order to the procedure described previously herein for assembly.

With reference to FIG. 16, prior to locking the insert 14 against the shank head 8, the shank 4 may be pivoted to a plurality of potentially desirable positions with respect to the receiver 10, followed by locking of the polyaxial mechanism by fully mating the multi-start closure top 19 with the receiver 10, followed by locking the rod in place with the set screw 20.

With reference to FIGS. 17 and 18, an alternative two-start closure of an embodiment of the invention, generally 218, is illustrated having a lower substantially cylindrical plug or body 230 and an upper integral break-off head 232. The body 230 includes an outer helically wound flange form guide and advancement structure 242 (dual start) that operably joins with the guide and advancement flange form structure 43 disposed on the arms of the receiver 10 or other receiver structure. It is foreseen that the dual-start closure guide and advancement structure 242 could alternatively be in the form of a buttress thread, a square thread, a reverse angle thread or other thread-like or non-thread-like helically wound advancement structure, for operably guiding under rotation and advancing the closure 218 downward between the receiver 10 or other receiver arms and having such a nature as to resist splaying of the arms when the closure 218 is advanced into the receiver channel. As shown in FIG. 17, the illustrated closure structure 218 also includes the break-off head 232 having a hex shape sized and shaped for cooperation with a socket-type tool. The head 232 is designed to break from the body 230 of the closure at a preselected torque, for example, 70 to 140 inch pounds. The closure body 230 includes a top surface 244 and an internal drive 246 formed therein that defines an aperture and is illustrated as a star-shape, such as that sold under the trademark TORX, or may be, for example, a hex drive or other internal drives such as slotted, tri-wing, spanner, two or more apertures of various shapes, and the like. A driving tool (not shown) sized and shaped for engagement with the internal drive 246 may be used for both rotatable disengagement of the closure 218 from the receiver arms, and re-engagement, if required. A base or bottom surface 247 of the closure is planar and further includes a central dome or nub 248 for gripping of a rod (either pressing directly downwardly on a rod or orienting a smaller rod toward one side of a compression insert) or for pressing into a deformable rod. In other embodiments, closure tops may include central points and/or spaced outer rims for engagement and penetration into rod or other longitudinal connecting member outer surfaces. It is noted that in some embodiments, the closure bottom surface does not include a nub, point, or rim. In some embodiments, the closure may further include a cannulation through bore extending along a central axis thereof, opening at the drive feature and extending through the bottom surfaces thereof. Such a through bore provides a passage through the closure interior for a length of wire (not shown) inserted therein to provide a guide for insertion of the closure top into the receiver arms.

With particular reference to FIG. 18, it is noted that the illustrated flange form structure 242 is a dual start structure that has a flange form depth D' measured from a root to a crest of the flange form 242 of between about 0.7 and about 0.8 millimeters. The flange form structure 242 further has a pitch P' (axial distance between flange forms, for example, as shown in FIG. 17 of about 0.100 inches. Returning to FIG. 18, the flange form structure 242 also has a splay control ramp surface 256 (shown extended as a line T' in phantom) that is disposed at an angle R' of about eighty degrees with respect to a radius or reference line X' perpendicular to a central axis of the closure 218. It is noted that with such a geometry, particularly with such a large pitch, a desirable material for the closure structure 218 is a cobalt chrome alloy so as to counter possible loosening that may occur under cyclical loading. If the structure 218 is made from cobalt chrome, a desirable material for a cooperating receiver is less hard than cobalt chrome, for example, stainless steel, titanium or a titanium alloy.

Figure 19:
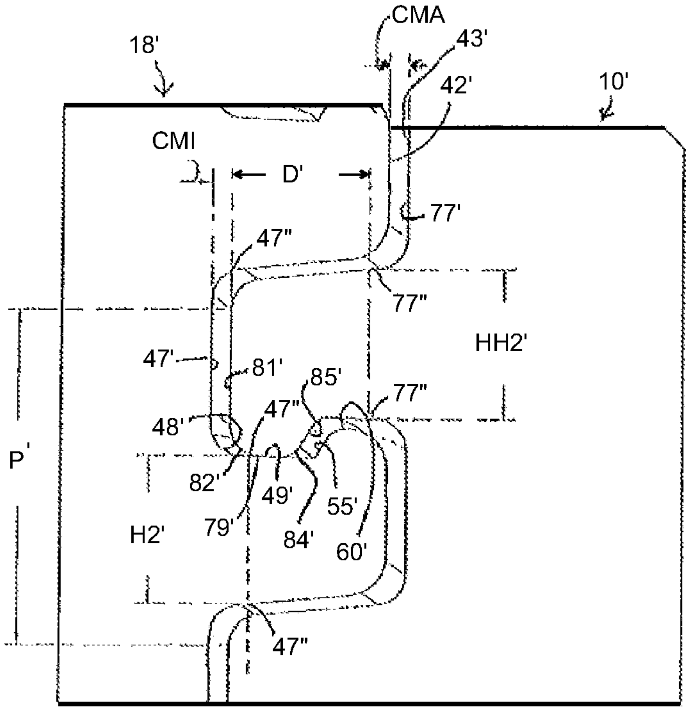
FIG. 19 is an enlarged and partial broken-away version of another embodiment of a splay control closure according to the invention.
Figure 20:
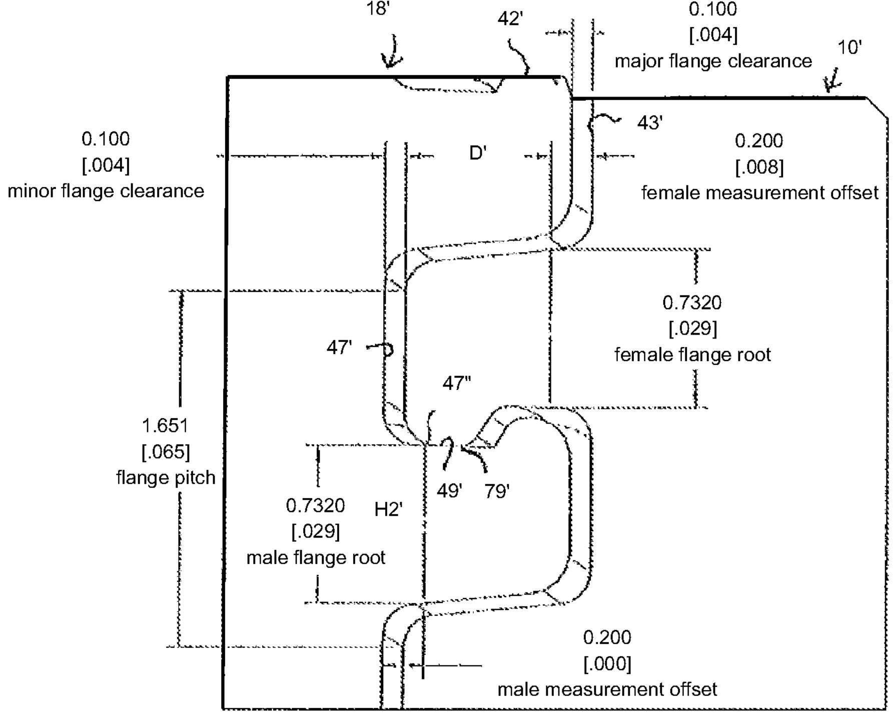
FIG. 20 is another enlarged and partial broken-away version of the closure of FIG. 19.

With reference to FIG. 19, another flange form arrangement according to an embodiment of the invention is shown having a closure 18' with a male flange form structure 42' and a receiver 10' with a female closure structure 43'. Although not necessarily identical, the structures 42' and 43' have surfaces that function similarly to respective structures 42 and 43 and thus similar surface will be identified by the same reference numeral and a " " will be added for identification purposes in this application. Thus, similar to the previously discussed structures 42 and 43, each flange form 42' includes several surfaces or contours that helically wrap about a central axis of the closure 18', for example, similar to the closure shown in FIG. 1. The contours of the flange form 42' include a root surface 47' that is helical and disposed substantially parallel to the closure central axis. Similar to the surface 47 described previously herein, the surface 47' may be understood as defining a virtual cylinder formed by a minor radius of the closure (radial distance between the closure central axis and the surface 47'). Adjacent the root surface 47' is a radiused surface, curve or corner surface 48' that in turn is adjacent to a load or loading surface or flank 49'. The flange form 42' further includes a splay control ramp 55' and an upper rounded or radiused surface 60'. Similarly, with respect to the cooperating female or receiver flange form 43', such form includes a load flank 79', a crest surface 81', a radiused corner surface 82', an opposed radiused surface 84' and a splay control ramp 85'. It is noted, that in operation, because of the radiused surface 48' of the flange form 42' and the receiver flange form radiused surface 82', an operational root location 47" is defined that is spaced outwardly radially from the surface 47' and is a first location wherein the cooperating flange form loading surfaces or flanks 49' and 79' can engage. A height H2' of the flange form 42' is defined as an axial height of such flange form located along the operational root 47". Similarly, the female or receiver flange form 43' has a height HH2' defined as an axial height of the form 43' located along an operational root 77" that is located radially inwardly of a root surface 77' of the flange form 43'. With further reference to FIG. 19, CMA identifies a major flange clearance and CMI identifies a minor flange clearance created by the cooperating radiused surfaces of the flange forms 42' and 43'. In the embodiment illustrated in FIG. 19, loading of the flange forms at surfaces 49' and 79' advantageously occurs at or substantially near the root 47" of the male or closure flange form 42'. Even during controlled splay of the form 43' (similar to what is shown and described with respect to FIGS. 9-13), loading of the flange forms 42' and 43' remains as close as possible to the male (closure)root location 47". A flange depth D' is also shown in FIG. 19 that shows a flange thickness taken between radiused surfaces that define clearances between the flange forms 42' and 43'. An axial distance or pitch P' is also shown in FIG. 19. FIG. 19 illustrates a ratio of D' to H2' (D'/H2') of less than 1. Such ratio is also shown in the enlarged FIG. 20 that further includes exemplary measurements for various parameters of the cooperating flange forms 42' and 43'. Such measurements are for example only and should not be considered as limiting the invention in any manner.

It is noted that as compared to conventional thread forms, even during a time of splay, contact between the loading surfaces 49' and 79' occurs and remains substantially near the operational root 47". In contrast in a square thread closure, for example, as splay occurs, overlapping of loading surfaces decreases and migrates until failure occurs. Also, with a square thread form, splay is not ultimately constrained by a splay control ramp as illustrated and described herein with respect to closures of the invention. Thus, in embodiments of the invention, splay is allowed and then ultimately constrained. This allows for a maximum thrust or downward force of the closure 18 or 18' against a rod for a given amount of torque. Flange forms according to embodiments of the invention also advantageously redirect splay forces diametrically across the closure 18 or 18', converting bending moment to tension, pulling opposed arms of the receiver (or receiver extension portions) toward one another during rotation of the closure between the receiver arms.

Figure 21:
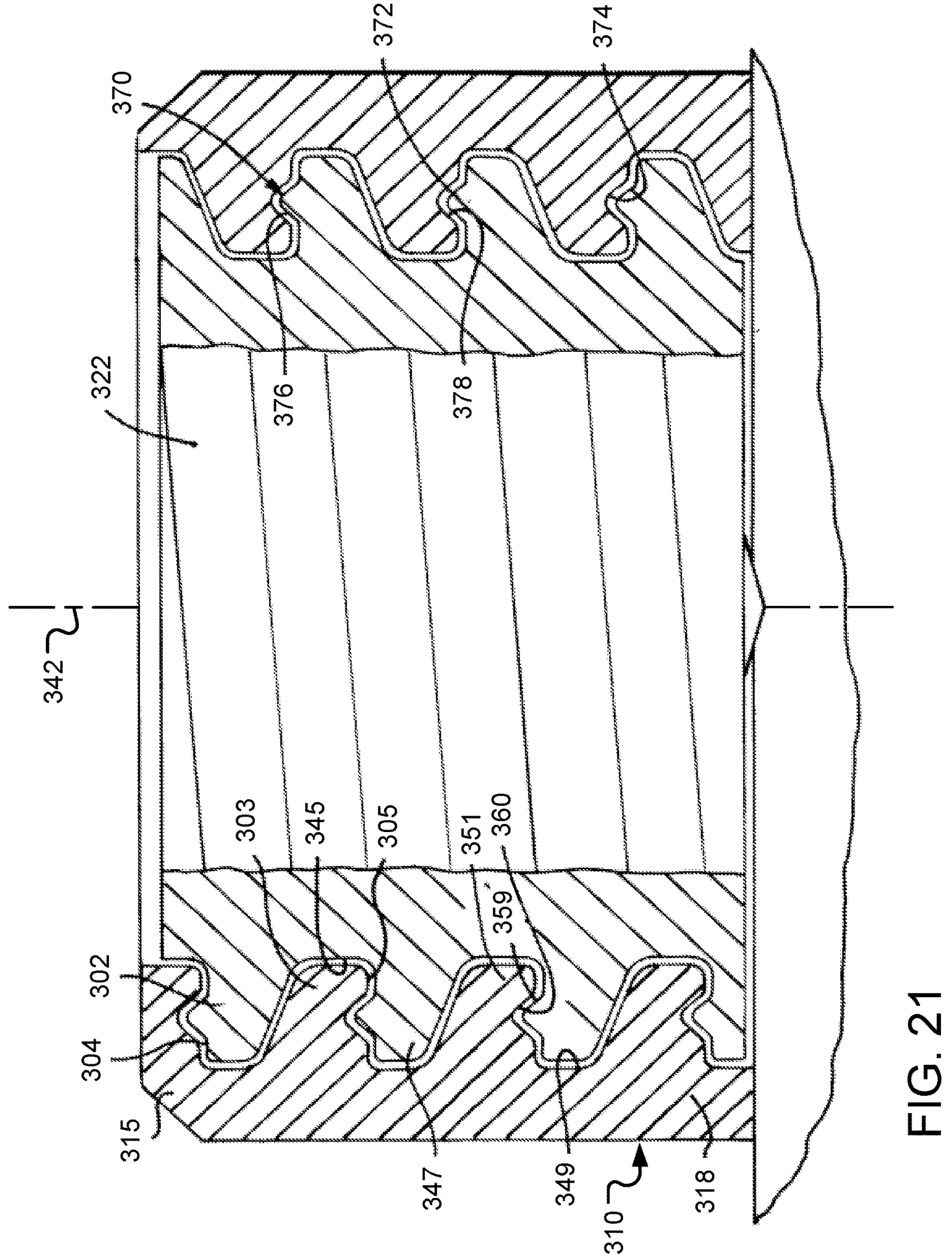
FIG. 21 illustrates details of a modified bone screw and closure showing a medial bead embodiment of an interlocking form of the present invention.

FIG. 21 illustrates a non-linear or compound thrust surface interlocking form arrangement 370 which is of a medial bead interlocking form type. The interlocking form arrangement 370 is a thrust surface 304 located on a plug 322 and internal interlocking form 303 with thrust surfaces 305 within a head 315 of a bone screw 310. The thrust surfaces 304 and 305 are contoured to provide complementary, interacting, splay resisting surfaces 359 and 360 on the external and internal interlocking forms 302 and 303 respectively. The external interlocking form 302 is provided with a bead 372 on the thrust surface 304, and the internal interlocking form 303 is provided with a complementary channel or groove 374 formed into the thrust surface 305. The illustrated thrust surfaces 304 and 305 are substantially perpendicular to the axis 342; however, such surfaces may alternatively be angled somewhat with respect to the axis 342 so as to slope downward or upward as the surface extends radially outward.

The bead 372 is located at a radius which is between or medial with respect to the root 345 and crest 347 of the external interlocking form 302. Similarly, the groove 374 is located at a radius which is medial to the root 349 and crest 351 of the internal interlocking form 303. The illustrated bead 372 and groove 374 are rounded and somewhat triangular in cross section. Alternatively, the bead and groove 372 and 374 could be pointed and triangular, squared off, or semicircular. It should also be noted that the bead and groove 372 and 374 could be replaced by a medial groove formed in the external interlocking form 302 on the thrust surface 304 and a medial bead formed on the thrust surface 305 of the internal interlocking form 303. An inwardly facing surface 376 of the bead 372 forms the splay resisting surface 359 thereof, while an outwardly facing surface 378 of the groove 374 forms the splay resisting surface of the groove 374. Engagement of the splay resisting surfaces 376 and 378, respectively of the bead 372 and groove 374, resists tendencies of the arms 318 of the screw head 315 to splay when the closure base 322 is rotated into the head 315.

Figures 22, 23, 24, 25:
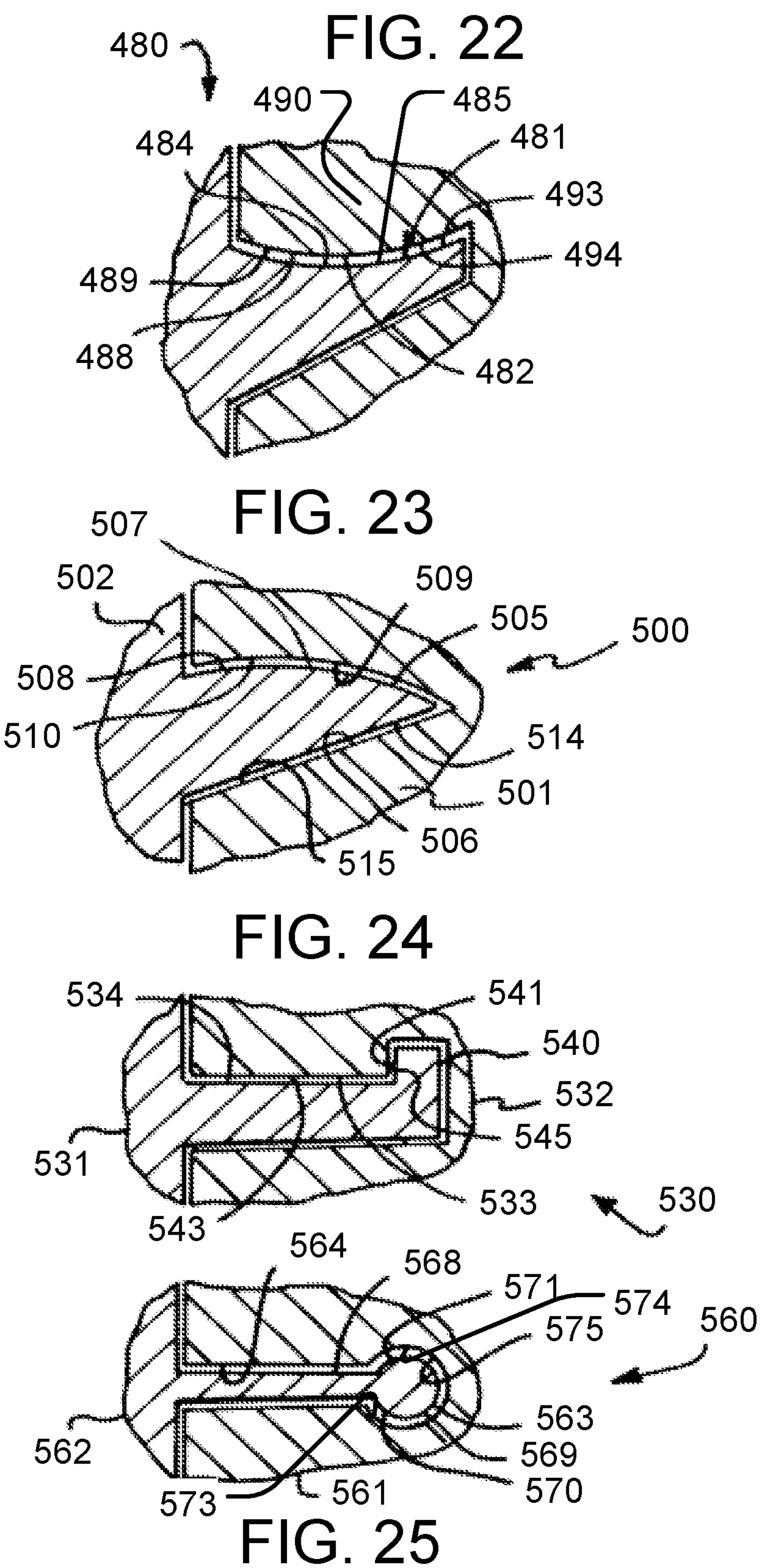
FIG. 22 is a fragmentary cross sectional view of a modified bone screw and closure, showing a pair of interlocking forms in accordance with the present invention.
FIG. 23 is a fragmentary cross sectional view of a modified embodiment of a bone screw and closure showing a pair of interlocking forms in accordance with the invention.
FIG. 24 is a fragmentary cross sectional view of a modified embodiment of a bone screw and closure showing a pair of interlocking forms in accordance with the invention.
FIG. 25 is a fragmentary cross sectional view of a modified embodiment of a bone screw and closure showing a pair of interlocking forms in accordance with the invention.

FIG. 22 illustrates a scalloped or scooped embodiment structure 480 including a pair of compound interlocking forms 481 and 482 according to the present invention. The interlocking form 481 is scalloped and, in effect, an inversion of the shallow rounded bead interlocking form similar to that of an earlier embodiment. The interlocking form 482 includes a shallow groove 484 formed in a thrust surface 485 of the external interlocking form 481 of a base 487 and a shallow bead 488 formed on a thrust surface 489 of the interlocking form 482 of a screw head 490. The groove 484 has a splay resisting surface 493 which cooperates with a complementary splay resisting surface 494 of the bead 488.

Illustrated in FIG. 23 is another guide and advancement structure 500 associated with a receiver member 501 and a closure member, such as a plug, 502 that is rotated into the receiver member 501. The structure 500 includes a first interlocking form 505 and a second interlocking form 506 attached to the closure member 502 and receiver member 501 respectively.

The first interlocking form 505 includes an arcuate upper surface 507 with a gripping or locking section 508. The second interlocking form 506 includes an arcuate lower surface 509 with a gripping or locking section 510. The interlocking forms 505 and 506 also have respective lower or leading surfaces 514 and 515 respectively that are sufficiently spaced to allow rotation about the axis thereof, but sufficiently close to be snug and not allow substantial movement of the forms 505 and 506 relative to each other in an axial direction without rotation.

FIG. 24 shows an alternative flange shaped embodiment of a guide and advancement structure 530 in accordance with the invention. The structure 530 is mounted on a closure 531 and a receiver 532 so that interlocking forms 533 and 534, which are seen in cross section, are helically mounted on the closure 531 and receiver 532 respectively.

The first interlocking form 533 is L or flange-shaped in cross section with a vertically or axially extending foot portion 540 with a gripping surface 541. The second interlocking form 534 generally complements the first and is also L or flange shaped except that a foot 543 thereof is much wider than the foot portion 540. The foot 543 has a gripping or wraparound surface 545 that abuts the surface 541 during assembly and resist radial movement between the receiver 532 and the closure 531.

Shown in FIG. 25 is another embodiment of a guide and advancement structure 560 in accordance with the invention. The structure 560 is utilized with a receiver 561 and a closure or plug 562. The structure 560 has first and second interlocking forms 563 and 564. The first interlocking form has an elongate wall 568 with a circular bead 569 attached to an end thereof opposite the closure 562. The bead 569 has opposed gripping surfaces 570 and 571. The second interlocking form 564 is shaped to mate with a generally surround the first interlocking form 563 except sufficient clearance is provided to allow the closure 562 to be rotated and advanced into the receiver 563 by sliding tangentially, but not radially. The second interlocking form 564 has a circular cross section channel 575 that receives the bead 569 and a pair of gripping surfaces 573 and 574 that engage and abut against the bead surfaces 570 and 571.

It is to be understood that while certain forms of the present invention have been illustrated and described herein, it is not to be limited to the specific forms or arrangement of parts described and shown.

What is claimed is:

1. A spinal fixation structure intended for use with an elongate rod, the spinal fixation structure comprising:

a receiver housing having a central bore defining an inner surface in an upper portion of the central bore with an open channel configured to receive the elongate rod, and upright arms having a discontinuous helically wound receiver thread formed therein, the discontinuous helically wound receiver thread having a receiver cylindrical root surface, a base height adjacent the receiver cylindrical root surface measured as an axial distance extending parallel with respect to a longitudinal axis of the receiver housing, a receiver linear load flank, and an opposed receiver linear stab flank; and a closure having a closure central axis, a cylindrical body including a top end having a top surface, a bottom end having a bottom surface opposite the top surface, a central internal drive structure extending into the cylindrical body centered along the closure central axis, and an outer complementary mating helically wound closure thread formed thereon and including a continuously wound closure linear load flank having a radially outwardly extending surface portion that angles upwardly toward the top end of the closure or extends perpendicularly relative to the closure central axis, a closure linear stab flank having a radially outwardly extending linear clearance surface portion, and a closure cylindrical root surface defining an outer surface of the cylindrical body and a base height adjacent the closure cylindrical root surface measured as an axial distance extending parallel with respect to the closure central axis with the base height of the receiver thread being substantially equal to the base height of the closure thread, wherein the closure thread has a thread pitch within a range of 0.040 inches and 0.070 inches, wherein the closure thread is configured to engage the receiver thread to secure the elongate rod within the open channel of the receiver housing in a locked configuration with an applied torque of at least 75 inch pounds to apply a locking thrust or a downward force of the closure against the rod;

wherein threaded engagement of the closure and the receiver housing is such that axial loading between the receiver load flank and the closure load flank up to the applied torque of at least 75 inch pounds causes the upright arms to splay outwardly relative to each other, wherein the outward splay of the upright arms initially increases with increasing torque, and then the outward splay is ultimately constrained by a rate of outward splay decreasing with further increasing torque, and wherein a clearance gap exists between the receiver linear stab flank and the closure linear stab flank when the spinal fixation structure is in the locked configuration.

2. The spinal fixation structure of claim 1, wherein the closure cylindrical root surface extends between an upper radiused surface communicating with the closure linear load flank and a lower radiused surface communicating with the closure linear stab flank.

3. The spinal fixation structure of claim 1, wherein the closure cylindrical root surface is parallel with respect to the closure central axis and helically wound around the cylindrical body of the closure.

4. The spinal fixation structure of claim 1, wherein the closure thread includes a thread crest having an outer cylindrical surface portion extending parallel relative to the central axis of the closure, wherein a lower end of the outer cylindrical surface portion joins with a curvilinear surface at an outer end of the radially outwardly extending linear clearance surface portion of the closure linear stab flank.

5. The spinal fixation structure of claim 4, wherein the mating helically wound closure thread further comprises a toe defined between the radially outwardly extending surface portion of the closure linear load flank and the thread crest, the toe angling upward from the radially outwardly extending surface portion of the closure linear load flank.

6. The spinal fixation structure of claim 1, wherein the bottom surface of the bottom end of the closure includes a central axial nub with a curvate surface protruding downward therefrom.

7. The spinal fixation structure of claim 1, further comprising a shank configured to be received in the receiver housing.

8. The spinal fixation structure of claim 7, wherein the shank comprises a partially spherically shaped head configured to pivotally engage a spherical seating surface in the receiver housing.

9. The spinal fixation structure of claim 8, wherein the shank comprises a longitudinal axis and a partially spherical shaped head has a top annular surface entirely surrounding an internal drive socket therein and extending perpendicularly with respect to the longitudinal axis.

10. The spinal fixation structure of claim 7, wherein the shank comprises a shank head having an internal drive socket and a central opening extending from the internal drive socket to a distal tip of the shank.

11. The spinal fixation structure of claim 1, wherein the base height of the mating helically wound closure thread extends between a first upper radiused surface communicating with the closure linear load flank and a first lower radiused surface communicating with the closure linear stab flank.

12. The spinal fixation structure of claim 1, wherein the base height of the receiver thread extends between a second upper radiused surface communicating with a receiver stab flank and a second lower radiused surface communicating with a receiver load flank.

13. The spinal fixation structure of claim 1, wherein the longitudinal axis of the receiver housing is aligned with the closure central axis.

14. The spinal fixation structure of claim 1, wherein the radially outwardly extending surface portion of the continuously wound closure linear load flank is at a load flank angle relative to a horizontal axis, the load flank angle being the same for an entirety of the continuously wound closure linear load flank.

15. The spinal fixation structure of claim 1, wherein the radially outwardly extending linear clearance surface portion of the closure linear stab flank is at a stab flank angle relative to a horizontal axis, the stab flank angle being the same for an entirety of the continuously wound closure linear stab flank.

16. The spinal fixation structure of claim 1, further comprising the elongate rod.

17. The spinal fixation structure of claim 16, wherein, in the locked configuration, the elongate rod is secured in position in the open channel of the receiver housing via the closure.

18. The spinal fixation structure of claim 1, wherein controlled splaying apart of the upright arms with axial loading is permitted up until the locked configuration is achieved.

19. The spinal fixation structure of claim 18, wherein the locked configuration is achieved when corresponding splay control ramps of the receiver housing and the closure, respectively, come into engagement so as to prevent splaying apart of the upright arms of the receiver housing.

20. The spinal fixation structure of claim 1, wherein the helically wound closure thread comprises a cylindrical crest surface extending parallel with respect to the closure central axis defining an outermost surface of the helically wound closure thread, an outer thread height defined as a vertical distance adjacent to the crest surface, and a closure thread depth defined as a horizontal distance between the crest surface thereof, wherein the outer thread height is substantially equal to the thread depth.

21. The spinal fixation structure of claim 20, wherein the difference between the outer thread height and the thread depth is less than 10% of the outer thread height.

22. The spinal fixation structure of claim 1, wherein the outward splay of the arms is evidenced by a first outward splay gap between the crest surface of the closure thread and the root surface of the receiver thread, wherein the outward splay increases with the first outward splay gap.

* * * * *